(12) United States Patent
Sato et al.

(10) Patent No.: US 8,934,695 B2
(45) Date of Patent: Jan. 13, 2015

(54) SIMILAR CASE SEARCHING APPARATUS AND SIMILAR CASE SEARCHING METHOD

(71) Applicant: Panasonic Corporation, Osaka (JP)

(72) Inventors: Yoshikuni Sato, Fukui (JP); Kenji Kondo, Kyoto (JP); Kazutoyo Takata, Osaka (JP); Kazuki Kozuka, Osaka (JP)

(73) Assignee: Panasonic Corporation, Osaka (JP)

( * ) Notice: Subject to any disclaimer, the term of this patent is extended or adjusted under 35 U.S.C. 154(b) by 71 days.

(21) Appl. No.: 13/903,243

(22) Filed: May 28, 2013

(65) Prior Publication Data

US 2013/0259350 A1 Oct. 3, 2013

Related U.S. Application Data

(63) Continuation of application No. PCT/JP2012/004886, filed on Aug. 1, 2012.

(30) Foreign Application Priority Data

Aug. 4, 2011 (JP) .................................. 2011-171317

(51) Int. Cl.
| | | |
|---|---|---|
| *G06K 9/00* | (2006.01) | |
| *G06T 7/00* | (2006.01) | |
| *G06Q 10/10* | (2012.01) | |
| *G06Q 50/24* | (2012.01) | |
| *G06F 19/00* | (2011.01) | |

(52) U.S. Cl.
CPC .............. *G06T 7/0014* (2013.01); *G06Q 10/10* (2013.01); *G06Q 50/24* (2013.01); *G06F 19/321* (2013.01); *G06F 19/3443* (2013.01)
USPC ........................................................ 382/131

(58) Field of Classification Search
None
See application file for complete search history.

(56) References Cited

U.S. PATENT DOCUMENTS

| | | |
|---|---|---|
| 8,180,123 B2 | 5/2012 | Oosawa et al. |
| 8,238,663 B2 | 8/2012 | Kato |

(Continued)

FOREIGN PATENT DOCUMENTS

| | | |
|---|---|---|
| JP | 2007-275408 | 10/2007 |
| JP | 2007-275440 | 10/2007 |

(Continued)

OTHER PUBLICATIONS

Müller, Henning, et al. "A review of content-based image retrieval systems in medical applications—clinical benefits and future directions." International journal of medical informatics 73.1 (2004): 1-23.*

(Continued)

*Primary Examiner* — Stephen R Koziol
*Assistant Examiner* — Raphael Schwartz
(74) *Attorney, Agent, or Firm* — Wenderoth, Lind & Ponack, L.L.P.

(57) ABSTRACT

A similar case searching apparatus includes: an image feature quantity extracting unit which extracts image feature quantities from an interpretation target image; a reference expression extracting unit which extracts a reference expression from a description related to a second test in a target image interpretation report; a weight determining unit which determines, for each image feature quantity, a weight which is larger as the correlation between the image feature quantity and the reference expression is higher, based on two-data correlation information; and a similar case searching unit which searches a case database for a similar case data item including a medical image similar to the interpretation target image, by weighting the image feature quantity extracted from the interpretation target image and a corresponding image feature quantity extracted from the medical image and comparing the weighted image feature quantities.

11 Claims, 19 Drawing Sheets

(56) References Cited

U.S. PATENT DOCUMENTS

| | | | |
|---|---|---|---|
| 2004/0003001 A1* | 1/2004 | Shimura | 707/104.1 |
| 2008/0215630 A1 | 9/2008 | Oosawa et al. | |
| 2009/0097756 A1 | 4/2009 | Kato | |

FOREIGN PATENT DOCUMENTS

| | | |
|---|---|---|
| JP | 2007-286945 | 11/2007 |
| JP | 2008-217363 | 9/2008 |
| JP | 2009-082442 | 4/2009 |
| JP | 2009-093563 | 4/2009 |
| JP | 2011-048672 | 3/2011 |
| JP | 2011-118543 | 6/2011 |

OTHER PUBLICATIONS

Worring, Marcel, Arnold Smeulders, and Simone Santini. "Interaction in content-based image retrieval: An evaluation of the state-of-the-art." Advances in Visual Information Systems. Springer Berlin Heidelberg, 2000. 26-36.*

International Search Report issued Sep. 11, 2012 in International (PCT) Application No. PCT/JP2012/004886.

Mitsutaka Nemoto et al., "Improvement of Tumor Detection Performance in Mammograms by Feature Selection from a Large Number of Features and Proposal of Fast Feature Selection Method", the transactions of the Institute of Electronics, Information and Communication Engineers, D- II , vol. J88-D-II , No. 2, Feb. 1, 2005, pp. 416-426, with partial English translation.

Misato Tamura et al., "Improvement of an extraction method of liver regions based on gray pattern of abnormal regions (2nd Report) ", The Institute of Electronics, Information and communication Engineers, Technical Report of IEICE, vol. 104, No. 580, p. 7-12, Jan. 15, 2005.

Junya Nakagawa et al., "Development of an automated extraction method for liver tumors in three dimensional abdominal CT images", The Institute of Electronics, Information and communication Engineers, Technical Report of IEICE (Sep. 2002).

MeCab (http://mecab.sourceforge.net), Sep. 27, 2009.

ChaSen(http://chasen-legacy.sourceforge.jp), Oct. 13, 2007.

KNP(http://nlp.kuee.kyoto-u.ac.jp/nl-resource/knp.html), Oct. 6, 2011.

CaboCha(http://chasen.org/~taku/software/cabocha/), Jun. 2001.

Naoki Kato et al., "Data Mining and its Applications", Asakura Publishing Co., Ltd., Sep. 25, 2008.

* cited by examiner

Early stain is observed in liver segment S3. In late phase, equal absorption with hepatic mesenchymal is observed, resulting in unclearness. T2 high signal is shown in MR, and thus angioma is suspicious.

FIG. 5A

| Image interpretation item |
|---|
| Early stain |
| Equal absorption |

FIG. 5B

| Reference expression |
|---|
| MR - T2 High signal |

FIG. 5C

| Disease name |
|---|
| Angioma |

FIG. 6

| Image interpretation item | Location | Time phase |
|---|---|---|
| Early stain | Liver segment S3 | — |
| Equal absorption | — | Late phase |

FIG. 7

| Image interpretation item | Location | Time phase |
|---|---|---|
| Early stain | Liver segment S3 | Early phase |
| Equal absorption | Liver segment S3 | Late phase |

FIG. 13

|  | Test 1 | | | ... | Test M | | |
| --- | --- | --- | --- | --- | --- | --- | --- |
|  | Image feature quantity 1 | Image feature quantity 2 | ... | Image feature quantity $N_{F1}$ | ... | Image feature quantity 1 | Image feature quantity 2 | ... | Image feature quantity $N_{FM}$ |
| Image interpretation item 1 | 0.808 | 0.627 | ... | 0.304 | ... | 0.781 | 0.573 | ... | 0.681 |
| Image interpretation item 2 | 0.372 | 0.991 | ... | 0.782 | ... | 0.329 | 0.684 | ... | 0.283 |
| ... | ... | ... | ... | ... | ... | ... | ... | ... | ... |
| Image interpretation item $N_{II}$ | 0.166 | 0.237 | ... | 0.724 | ... | 0.254 | 0.789 | ... | 0.384 |
| Image interpretation item 1 | 0.602 | 0.638 | ... | 0.222 | ... | 0.794 | 0.382 | ... | 0.399 |
| Image interpretation item 2 | 0.304 | 0.885 | ... | 0.719 | ... | 0.981 | 0.429 | ... | 0.784 |
| ... | ... | ... | ... | ... | ... | ... | ... | ... | ... |
| Image interpretation item $N_R$ | 0.022 | 0.254 | ... | 0.864 | ... | 0.784 | 0.678 | ... | 0.690 |

FIG. 14

|  | Test 1 | | | ... | Test M | | | |
| --- | --- | --- | --- | --- | --- | --- | --- | --- |
|  | Image feature quantity 1 | Image feature quantity 2 | ... | Image feature quantity $N_F$ | ... | Image feature quantity 1 | Image feature quantity 2 | ... | Image feature quantity $N_{FM}$ |
| Disease name 1 | 0.671 | 0.697 | ... | 0.191 | ... | 0.638 | 0.319 | ... | 0.543 |
| Disease name 2 | 0.726 | 0.062 | ... | 0.785 | ... | 0.262 | 0.339 | ... | 0.608 |
| Disease name 3 | 0.365 | 0.129 | ... | 0.695 | ... | 0.904 | 0.774 | ... | 0.204 |
| ... | ... | ... | ... | ... | ... | ... | ... | ... | ... |
| Disease name $N_D$ | 0.277 | 0.238 | ... | 0.818 | ... | 0.804 | 0.639 | ... | 0.548 |

FIG. 15

| | Disease name 1 | Disease name 2 | Disease name 3 | ... | Image feature quantity $N_D$ |
|---|---|---|---|---|---|
| Image interpretation item 1 | 23.06 | 47.58 | 9.58 | ... | 5.10 |
| Image interpretation item 2 | 1.41 | 6.21 | 32.96 | ... | 12.80 |
| ... | ... | ... | ... | ... | ... |
| Image interpretation item $N_{II}$ | 36.35 | 22.52 | 16.82 | ... | 23.94 |
| Image interpretation item 1 | 18.67 | 10.23 | 9.66 | ... | 15.15 |
| Image interpretation item 2 | 0.98 | 1.26 | 3.34 | ... | 2.59 |
| ... | ... | ... | ... | ... | ... |
| Image interpretation item $N_R$ | 19.07 | 21.07 | 38.48 | ... | 3.58 |

SIMILAR CASE SEARCHING APPARATUS AND SIMILAR CASE SEARCHING METHOD

CROSS REFERENCE TO RELATED APPLICATIONS

This is a continuation application of PCT International Application No. PCT/JP2012/004886 filed on Aug. 1, 2012, designating the United States of America, which is based on and claims priority of Japanese Patent Application No. 2011-171317 filed on Aug. 4, 2011. The entire disclosures of the above-identified applications, including the specifications, drawings and claims are incorporated herein by reference in their entirety.

FIELD

Apparatuses and methods consistent with an exemplary embodiment of the present disclosure relate generally to similar case searching apparatuses and similar case searching methods for searching out a similar case that is useful as a reference for an interpretation of an image for medical use (a medical image).

BACKGROUND

Recent development and wide spread use of medical image capturing apparatuses for Computed Tomography (CT) and Magnetic Resonance Imaging (MRI) have made it possible to obtain a large volume of high-definition digital images for medical use. Furthermore, medical images already interpreted by doctors who are image interpreters are increasingly accumulated one by one together with the image interpretation reports thereof in Picture Archiving and Communication Systems (PACS). In order to interpret a target image with reference to medical images similar to the target image, a start is made for development of techniques for searching out the similar images (medical images) from already-accumulated past cases.

In general, a doctor performs a plurality of tests and considers the results when making an actual diagnosis. In this situation, needs have been created for similar case searches in which images obtained from different modalities are included or information of time-series changes is included.

Patent Literature 1 discloses an apparatus which performs similar case searches using a plurality of test results. In Patent Literature 1, such similar case searches are performed that satisfy the following three conditions: the same image capturing scheme as in a current target case is used; the same test is performed to obtain information between similar cases; and image features are similar to those of the current target image. In the Patent Literature 1, the tests indicate modalities such as a CT apparatus and an MRI apparatus, and the image capturing schemes indicate image capturing approaches, image capturing conditions, image capturing protocols, and image capturing sequences. In Patent Literature 1, it is possible to narrow down many cases extracted in a test using only one of the current target images into a case having a higher similarity.

CITATION LIST

Patent Literature

PTL 1
Japanese Unexamined Patent Application Publication No, 2008-217363

SUMMARY

Technical Problem

In the aforementioned conventional configuration, searches are performed based on whether or not the tests and image capturing schemes are the same. For this reason, in such a conventional search, the intention of the test is not reflected. More specifically, it is problematic that user focus points on similarity in images obtained in a given test scheme cannot be reflected in the conventional search.

One non-limiting and exemplary embodiment disclosed herein provides a similar case searching apparatus capable of performing similar case searches in which user focus points are reflected and information obtained in tests performed by different modalities or information of time-series changes is included.

Solution to Problem

In order to solve the aforementioned problem, a similar case searching apparatus according to an aspect of the present disclosure is a similar case searching apparatus which searches a case database for a similar case data item similar to a target case data item of a target case to be diagnosed, the case database storing a plurality of case data items, each of the case data items and the target case data item including one or more medical images and an image interpretation report that is a document data item indicating a result of interpreting the one or more medical images, the similar case searching apparatus including: an image feature quantity extracting unit configured to extract a plurality of image feature quantities from an interpretation target image which is a medical image and obtained by carrying out a first test on a subject; a report analyzing unit configured to analyze a target image interpretation report which is generated by a user in interpretation of the interpretation target image, and divide descriptions in the target image interpretation report into a description related to the first test and a description related to a second test different from the first test carried out on the subject of the first test; a reference expression extracting unit configured to extract, from the description related to the second test divided by the report analyzing unit, one or more reference expressions each of which is a character string indicating a feature of a medical image, each of the reference expressions indicating a feature of a reference image obtained by carrying out the second test on the subject of the first test; a weight determining unit configured to determine, for each of the image feature quantities extracted from the interpretation target image by the image feature quantity extracting unit, a weight based on two-data correlation information that is prepared information defining a correlation between each of image feature quantities extracted from one or more medical images and each of one or more reference expressions extracted from an image interpretation report of the one or more medical images, the weight to the extracted image feature quantity having a value that is larger as the correlation between the image feature quantity and the reference expression is higher; and a similar case searching unit configured to search the case database for the similar case data item including a similar image similar to the interpretation target image, by weighting each of the image feature quantities in a first set extracted from the interpretation target image by the image feature quantity extracting unit and a corresponding one of the image feature quantities in a second set extracted from the one or more medical images included in the case data item registered in the case database, using the weight to each of the image feature quantities determined by the weight determining unit, and comparing the weighted image feature quantities in the first set and the weighted image feature quantities in the second set.

It is to be noted that an embodiment of the present disclosure may be implemented or realized as a system, a method, an integrated circuit, a computer program, or a computer-readable recording medium such as CD-ROMs, and that the embodiment may be implemented or realized as an arbitrary combination of (parts of) a system, a method, an integrated circuit, a computer program, or a recording medium.

Additional benefits and advantages of the disclosed embodiment will be apparent from the Specification and Drawings. The benefits and/or advantages may be individually obtained by the embodiment and features of the Specification and Drawings, which need not all be provided in order to obtain one or more of such benefits and/or advantages.

Advantageous Effects

According to an embodiment of the present disclosure, it is possible to provide a similar case searching apparatus capable of performing similar case searches in which user focus points on similar image searches are reflected and information items obtained in tests performed by a plurality of different modalities or information items indicating time-series changes are included.

BRIEF DESCRIPTION OF DRAWINGS

These and other advantages and features will become apparent from the following description thereof taken in conjunction with the accompanying Drawings, by way of non-limiting examples of an embodiment disclosed herein.

FIG. 5A is a table of image interpretation items extracted from the image interpretation report according to the embodiment.

FIG. 5B is a table of a reference expression extracted from the image interpretation report according to the embodiment.

FIG. 5C is a table of a disease name extracted from the age interpretation report according to the embodiment.

FIG. 6 is a table of image interpretation items extracted from the image interpretation report according to the embodiment, and a location and a time phase extracted together with the image interpretation items.

FIG. 7 is a table of image interpretation items extracted from the image interpretation report according to the embodiment, and locations and time phases extracted together with the image interpretation items by performing context interpretation.

FIG. 13 is a table (a storage format) of the correlations between image feature quantities and image interpretation items as image interpretation knowledge according to the embodiment.

FIG. 14 is a table (a storage format) of the correlations between image feature quantities and disease names extracted as image interpretation knowledge according to the embodiment.

FIG. 15 is a table (a storage format) of the correlations between image interpretation items and disease names extracted as image interpretation knowledge according to the embodiment.

DESCRIPTION OF EMBODIMENT

Figure 1:
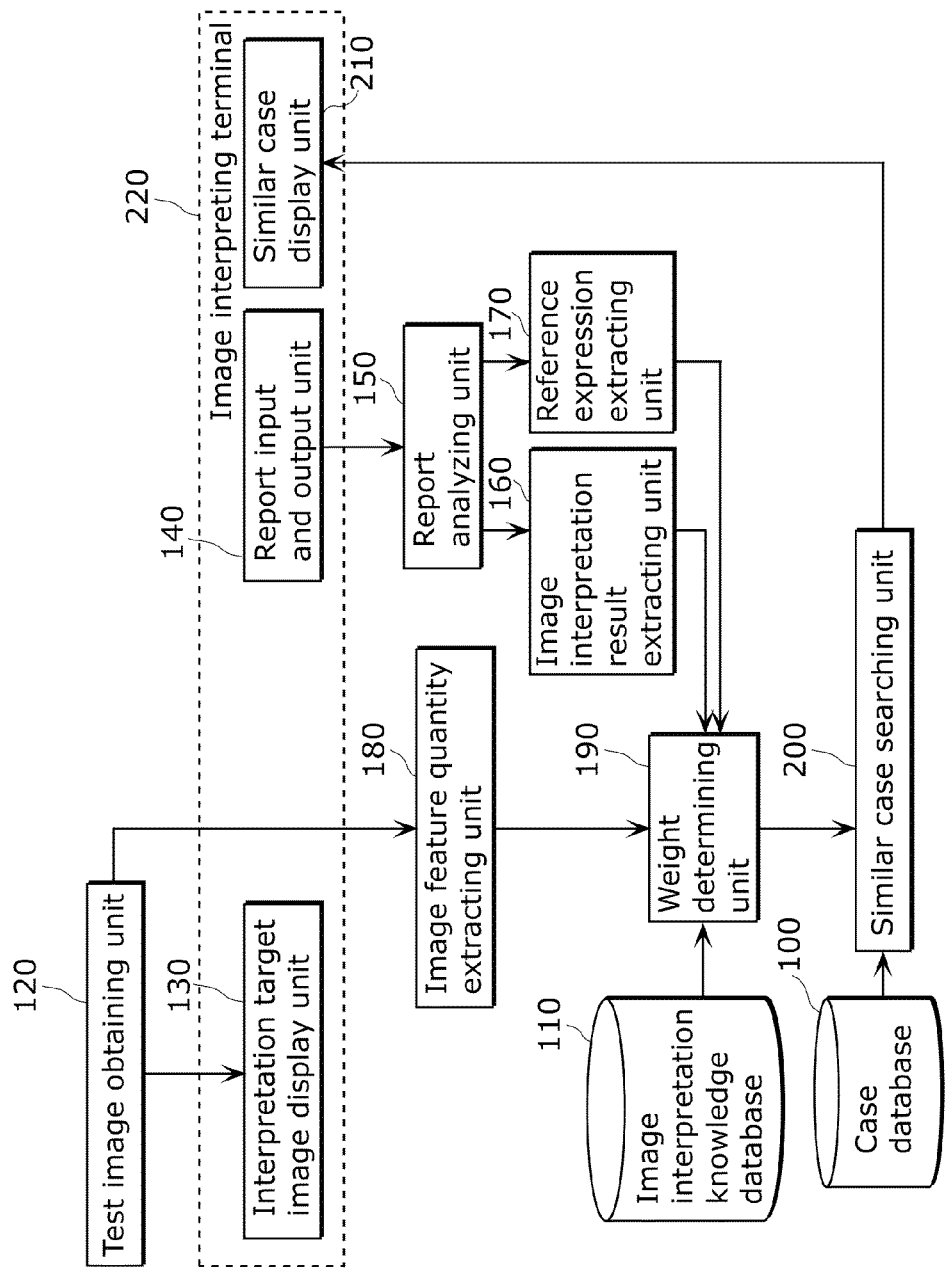
FIG. 1 is a block diagram of a structure of a similar case searching apparatus according to an embodiment of the present disclosure.

A similar case searching apparatus according to an aspect of the present disclosure is a similar case searching apparatus which searches a case database for a similar case data item similar to a target case data item of a target case to be diagnosed, the case database storing a plurality of case data items, each of the case data items and the target case data item including one or more medical images and an image interpretation report that is a document data item indicating a result of interpreting the one or more medical images, the similar case searching apparatus including: an image feature quantity extracting unit configured to extract a plurality of image feature quantities from an interpretation target image which is a medical image and obtained by carrying out a first test on a subject; a report analyzing unit configured to analyze a target image interpretation report which is generated by a user in interpretation of the interpretation target image, and divide descriptions in the target image interpretation report into a description related to the first test and a description related to a second test different from the first test carried out on the subject of the first test; a reference expression extracting unit configured to extract, from the description related to the second test divided by the report analyzing unit, one or more reference expressions each of which is a character string indicating a feature of a medical image, each of the reference expressions indicating a feature of a reference image obtained by carrying out the second test on the subject of the first test; a weight determining unit configured to determine, for each of the image feature quantities extracted from the interpretation target image by the image feature quantity extracting unit, a weight based on two-data correlation information that is prepared information defining a correlation between each of image feature quantities extracted from one or more medical images and each of one or more reference expressions extracted from an image interpretation report of the one or more medical images, the weight to the extracted image feature quantity having a value that is larger as the correlation between the image feature quantity and the reference expression is higher; and a similar case searching unit configured to search the case database for the similar case data item including a similar image similar to the interpretation target image, by weighting each of the image feature quantities in a first set extracted from the interpretation target image by the image feature quantity extracting unit and a corresponding one of the image feature quantities in a second set extracted from the one or more medical images included in the case data item registered in the case database, using the weight to each of the image feature quantities determined by the weight determining unit, and comparing the weighted image feature quantities in the first set and the weighted image feature quantities in the second set.

With this structure, each of the image feature quantities is assigned with the weight based on the reference expression extracted from the target image interpretation report, and the similar case search is performed based on the weighted image feature quantity. In other words, comparatively large weights are added to the image feature quantities related to the extracted reference expression, and comparatively small weights are added to the image feature quantities not related to the same. The use of the reference expression makes it possible to perform the weighting based on the description regarding the other test performed onto the same subject. In this way, it is possible to perform the similar case search in which the user focus points are reflected and the information items obtained in the tests performed by the plurality of different modalities or thee information items indicating such time-series changes are included.

More specifically, the report analyzing unit may be configured to divide, as the description related to the second test, a description related to a medical image capturing apparatus different from a medical image capturing apparatus used in the first test, from the interpretation target report.

With this structure, it is possible to perform the similar case search in which the user focus points are reflected and the information items obtained in the tests performed by the plurality of different modalities are included.

In addition, the report analyzing unit may be configured to divide, as the description related to the second test, a description related to a test carried out in the past, from the interpretation target report.

With this structure, it is possible to perform the similar case search in which the user focus points are reflected and the information items of the time-series changes are included.

In addition, the similar case searching apparatus may further include: an image interpretation result extracting unit configured to extract, from the description related to the first test divided by the report analyzing unit, one or more image interpretation items each of which is a character string indicating a feature of a medical image, each of the image interpretation items indicating a feature of the interpretation target image obtained by carrying out the first test on the subject, wherein the two-data correlation information further indicates a correlation between each of the image feature quantities extracted from the one or more medical images and each of the image interpretation items extracted from the image interpretation report related to the one or more medical images, and the weight determining unit is configured to determine, for each of the image feature quantities extracted from the interpretation target image by the image feature quantity extracting unit, a weight based on the two-data correlation information, the weight having a value that is larger as the correlation between the image feature quantity and the image interpretation item extracted by the image interpretation result extracting unit or the reference expression extracted by the reference expression extracting unit is higher.

With this structure, each of the image feature quantities is assigned with the weight based on the image interpretation item or the reference expression extracted from the target image interpretation report, and the similar case search is performed based on the weighted image feature quantity. In other words, the comparatively large weights are added to the image feature quantities related to the extracted image interpretation item or reference expression, and the comparatively small weights are added to the image feature quantities not related to the same. In addition, the use of the reference expression makes it possible to perform the weighting based on the description regarding the other test performed onto the same subject. In this way, it is possible to perform the similar case search in which the user focus points are reflected and the information items obtained in the tests performed by the plurality of different modalities or the information items indicating the time-series changes are included.

In addition, the image interpretation result extracting unit may be further configured to extract one or more disease names each of which is a result of a diagnosis made by the user from the description related to the first test, the two-data correlation information may further indicate a correlation between each of the image feature quantities extracted from the one or more medical images and each of the disease names extracted from the image interpretation report related to the one or more medical images, and the weight determining unit may be configured to determine, for each of the image feature quantities extracted from the interpretation target image by the image feature quantity extracting unit, a weight based on the two-data correlation information, the weight having a value that is larger as the correlation between the image feature quantity and one of the image interpretation item or the disease name extracted by the image interpretation result extracting unit and the reference expression extracted by the reference expression extracting unit is higher.

With this structure, it is possible to add the weight to each of the image feature quantities based on the disease name extracted from the target image interpretation report. In this way, it is possible to perform the similar case search in which the disease name is considered.

In addition, when the image interpretation result extracting unit extracts the disease name from the description related to the first test, the weight determining unit may be configured to determine, for each of the image feature quantities extracted from the interpretation target image by the image feature quantity extracting unit, a weight based on the two-data correlation information, the weight having a value that is larger as the correlation between the image feature quantity and the disease name extracted by the image interpretation result extracting unit is higher.

With this structure, it is possible to perform the appropriate similar case search in the state where the user cannot make determinations on which one or more image interpretation items are the bases for the estimation of the disease name made based on user's intuition or the like. The user can get a hint for the bases (image interpretation items) for the diagnosis as a result of the similar case search.

In addition, the two-data correlation information may further indicate a correlation between each of the image interpretation items and each of the disease names which are extracted from the image interpretation report, and when (i) the image interpretation result extracting unit extracts the one or more disease names from the description related to the first test and (ii) the image interpretation result extracting unit extracts the one or more image interpretation items from the description related to the first test or the reference expression extracting unit extracts the one or more reference expressions from the description related to the second test, the weight determining unit may be configured to determine, for each of the image feature quantities extracted from the interpretation target image by the image feature quantity extracting unit, a weight based on the two-data correlation information, the weight having a value that is a product of (i) a value indicating the correlation between the image feature quantity and the image interpretation items extracted by the image interpretation result extracting unit or the reference expression extracted by the reference expression extracting unit and (ii) a value indicating the correlation between the image interpretation items or the reference expression and the disease name extracted by the image interpretation result extracting unit.

With this structure, when the disease name, the image interpretation item or the reference expression are written in the target image interpretation report, it is possible to perform the similar case search in which the correlation between the image feature quantity and the image interpretation item or the reference expression and the correlation between the disease name and the image interpretation item or the reference expression are evaluated at the same time.

In addition, when (i) the image interpretation result extracting unit extracts one of the image interpretation items from the description related to the first test or (ii) the reference expression extracting unit extracts one of the reference expressions from the description related to the second test, the weight determining unit may be configured to determine, for each of the image feature quantities extracted from the interpretation target image by the image feature quantity extracting unit, a weight based on the two-data correlation information, the weight having a value indicating the correlation between the image feature quantity and the image interpretation item extracted by the image interpretation result extracting unit or the reference expression extracted by the reference expression extracting unit.

With this structure, it is possible to perform the appropriate similar case search in the state where the user cannot make a definitive diagnosis including the disease name although the user was able to determine the image interpretation item or the reference expression that should be focused on and wishes to make the definitive diagnosis based on a hint that is obtainable as a result of the similar case search.

In addition, each of case data items registered in the case data base may further include a reference image obtained by carrying out the second test on the subject of the first test, the image feature quantity extracting unit may be further configured to extract a plurality of image feature quantities from the reference image, the weight determining unit may be further configured to determine, for each of the image feature quantities extracted from the reference image by the image feature quantity extracting unit, a weight based on the two-data correlation information, the weight having a value that is larger as the correlation between the image feature quantity and the image interpretation item extracted by the image interpretation result extracting unit or the reference expression extracted by the reference expression extracting unit is higher, and the similar case searching unit may be configured to search the case database for the similar case data item including similar images similar to the interpretation target image and the reference image, by weighting each of the image feature quantities in a first set extracted from the interpretation target image and the reference image by the image feature quantity extracting unit and the corresponding one of the image feature quantities in a second set extracted from the medical images included in the case data item registered in the case database, using the weight to the image feature quantity determined by the weight determining unit, and comparing the weighted image feature quantities in the first set and the weighted image feature quantities in the second set.

With this structure, when the case data items including the plurality of medical images and the image interpretation reports are registered in the case database, it is possible to perform the similar case search by comparing the medical images included in the respective case data items with each other. In other words, it is possible to perform the similar case search in which the user focus points are reflected and the medical images captured in the other test are integrated.

It is to be noted that the embodiment of the present disclosure may be implemented or realized as a system, a method, an integrated circuit, a computer program, or a computer-readable recording medium such as CD-ROMs, and that the embodiment may be implemented or realized as an arbitrary combination of (parts of) a system, a method, an integrated circuit, a computer program, or a recording medium.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, a certain exemplary embodiment is described in greater detail with reference to the accompanying Drawings.

The exemplary embodiment described below shows a general or specific example. The numerical values, shapes, materials, structural elements, the arrangement and connection of the structural elements, steps, the processing order of the steps etc. shown in the following exemplary embodiment are mere examples, and therefore do not limit the scope of the appended Claims and their equivalents. Therefore, among the structural elements in the following exemplary embodiment, structural elements not recited in any one of the independent claims are described as arbitrary structural elements.

Hereinafter, an exemplary embodiment of the present disclosure is described with reference to the Drawings.

The embodiment described below shows an example of the present disclosure. The numerical values, shapes, materials, structural elements, the arrangement and connection of the structural elements, steps, the processing order of the steps etc. shown in the following embodiment are mere examples, and therefore do not limit the scope of the inventive concept, the scope of which is defined in the appended Claims and their equivalents. Among the structural elements in the following embodiment, the structural elements not recited in any one of the independent Claims defining the most generic concept in the present disclosure are described as optional structural elements in the embodiment.

FIG. 1 is a block diagram of a structure of a similar case searching apparatus according to the embodiment of the present disclosure.

A similar case searching apparatus include a case database 100, an image interpretation knowledge database 110, a test image obtaining unit 120, an interpretation target image display unit 130, a report input and output unit 140, a report analyzing unit 150, an image interpretation result extracting unit 160, a reference expression extracting unit 170, an image feature quantity extracting unit 180, a weight determining unit 190, a similar case searching unit 200, and a similar case display unit 210.

The case database 100 is a database storing a plurality of case data items (hereinafter simply referred to as "cases"). Each of the case data items is composed of at least one medical image (in this Description, "image data" is simply referred to as an "image") and an image interpretation report that is the result of interpretation of the at least one medical image). Such a medical image is an image captured in Computer Tomography (CT), Magnetic Resonance Imaging (MRI), or the like. The image interpretation knowledge database 110 is a database storing image interpretation knowledge obtained by analyzing a plurality of cases. This image interpretation knowledge database 110 is described in detail later. The case database 100 and the image interpretation knowledge database 110 are stored in a recording device such as a Hard Disk Drive (HDD).

The test image obtaining unit 120 reads interpretation target images captured in a CT, MRI, or the like by a medical image capturing apparatus and other test images (reference images) of the same subject from the medical image capturing apparatus or a storage device that is externally connected. It is to be noted that the other test images may be obtained from the same hospital as the source of the interpretation target image, or may be obtained, via a network, from another hospital in which the subject experienced a test in the past.

The interpretation target image display unit 130 is composed of a medical-use high-definition monitor or the like, and displays the interpretation target image read by the test image obtaining unit 120.

The report input and output unit 140 is composed of an input device such as a keyboard and a mouse and a display device for allowing a user (such as a doctor) to confirm his or her inputs by displaying an image interpretation report portions input using the input device. The user inputs the image interpretation report portions through the report input and output unit 140 with reference to the interpretation target image displayed by the interpretation target image display unit 130.

The interpretation target image display unit 130, the report input and output unit 140, and the similar case display unit 210 that is described later constitute an image interpreting terminal 220.

The report analyzing unit 150 analyzes the image interpretation report input through the report input and output unit 140, and divides the descriptions included in the image interpretation report into descriptions of the interpretation target image that is currently being interpreted and descriptions of the other tests.

The image interpretation result extracting unit 160 extracts image interpretation items and determines them as text feature quantities. Here, each image interpretation item verbally indicates information read from a medical image by a doctor based on descriptions of an interpretation target image obtained from the report analyzing unit 150.

The reference expression extracting unit 170 analyses reference expressions to be described later from the descriptions of the other tests obtained from the report analyzing unit 150, and extracts them as test feature quantities.

The image feature quantity extracting unit 180 extracts a plurality of kinds of image feature quantities from all of medical images read by the test image obtaining unit 120.

The weight determining unit 190 determines weights to the respective image feature quantities to be used in image search, based on text feature quantities extracted by at least one of the image interpretation result extracting unit 160 and the reference expression extracting unit 170, image feature quantities extracted by the image feature quantity extracting unit 180, and the image interpretation knowledge stored in the image interpretation knowledge database 110.

The similar case searching unit 200 searches the case database 100 for a case including at least one medical image similar to the interpretation target image, utilizing the image feature quantities extracted by the image feature quantity extracting unit 180 and the weights determined by the weight determining unit 190.

The similar case display unit 210 displays the similar case searched out by the similar case searching unit 200. The similar case display unit 210 may be separately configured with a device of the same model as that of the high-definition monitor constituting the interpretation target image display unit 130. Here, the similar case display unit 210 and the interpretation target image display unit 130 may be different in their device models. Alternatively, the similar case display unit 210 and the interpretation target image display unit 130 may be configured with the same high-definition monitor. Furthermore, the interpretation target image and the similar case may be displayed on the high-definition monitor at the same time.

Hereinafter, operations performed by the respective units according to this embodiment are described in detail.

(Preparation of Image Interpretation Knowledge Database)

Prior to a similar case search, image interpretation knowledge is obtained in advance, and is stored in the image interpretation knowledge database 110. The image interpretation knowledge is generated to include a plurality of "cases" each of which is composed of at least one medical image and the image interpretation report that is obtained as a result of the interpretation of the at least one medical image. The similar case to be searched out and used here may be a case stored in the case database 100 storing cases and used to search for a similar case, or a case stored in another database. The number of cases required is the number that is sufficient to obtain a certain law and knowledge using various kinds of data mining algorithms. The number of data items is normally any number in a range from several hundreds to several tens of thousands. The image interpretation knowledge used in this embodiment is the correlation between two of three data types that are (i) the image feature quantity, (ii) the image interpretation item, and (iii) the disease name and the correlation between two of three data types that are (i) the image feature quantity, (ii) the reference expression, and (iii) the disease name.

The "image feature quantities" relate to, for example, the shapes of organs or lesion areas in medical images, or the luminance distributions of the medical images. For example, Non-patent Literature 1 describes the use of four hundred and ninety kinds of feature quantities ("improvement of Tumor Detection Performance in Mammograms by Feature Selection from a Large Number of Features and Proposal of Fast Feature Selection Method", by Nemoto, Shimizu, Hagihara, Kobatake, and Nawano, The Journal of the Institute of Electronics, Information and Communication Engineers (J. IEICE) D-H, Vol. J88-D-II, No, 2, pp. 416-426, February 2005). As image feature quantities used in this embodiment, several ten to several hundred kinds of image feature quantities are predefined for each of medical image capturing apparatuses (modalities) used to capture the medical images or each of target organs used for image interpretation.

An "image interpretation item" is defined in this Description as a "character string made by a user (such as a doctor) as verbally indicating a feature of an interpretation target image". Terms that are used as image interpretation items are limited within certain ranges for the respective medical image capturing apparatuses, target organs, or the like. Examples of the image interpretation items include; Lobular, Spinal, Irregular, Clear border, Unclear contour, Low density, High density, Low absorption, High absorption, Ground-glass opacity, Calcification, Mosaic pattern, Early stain, Low echo, High echo, and Fuzz.

In this Description, a "reference expression" is defined as a "character string indicating a feature of a medical image (reference image) obtained by carrying out a different test on a subject of a test carried out to obtain an interpretation target image included in the image interpretation report". The different test mentioned here may be a test performed by the same modality as the modality used to capture the interpretation target image that is currently being interpreted or a test performed by a different modality. In the former case, a reference expression corresponds to a keyword such as "X is increased compared with the one in the previous time". In the latter case, reference expressions correspond to keywords such as "MR—High signal" and "US—High echo" that appear in an image interpretation report in which the interpretation target image is a CT image. Here, US is an acronym of Ultra Sonic. Such a reference expression mainly describes, among information items in the other test, information that cannot be obtained only from the image that is currently being interpreted.

A "disease name" is the name of a disease diagnosed by the user (such as the doctor) based on medical images and other medical tests. The name of the disease diagnosed in the image interpretation may be different from the disease in the definitive diagnosis made after the other medical tests. Thus, the definitive diagnosis is used to generate the image interpretation knowledge database 110.

Hereinafter, a procedure for generating the image interpretation knowledge is described with reference to the flowchart of FIG. 2. It is assumed that the medical image capturing apparatus that is used in this embodiment is a multi-slice CT apparatus, and that a target organ and a target disease are a liver and a liver tumor, respectively.

In Step SW, a case is obtained from a database storing cases for obtaining image interpretation knowledge. A case is composed of medical images captured in a test for a disease currently being performed on a subject and an image interpretation report obtained as a result of the interpretation of all the medical images captured in all the tests for the disease performed on the subject in the past. When the medical images are obtained by the multi-slice CT apparatus, the case includes several slice images. In addition, in the tests performed by such a CT apparatus or an MRI apparatus, a contrast medium may be used. In one test using a contrast medium, images are captured several times at time intervals. In this case, many slice images are obtained in sets the number of which corresponds to the number of image capturing. Normally, when a doctor interprets such multi-slice CT images, one to several important slice images among the slice images are attached to the corresponding image interpretation report as key images. Hereinafter, a set of several slice images or several key images are simply referred to as "medical images" or "images".

In Step S11, image feature quantities are extracted from all the obtained medical images. The process in Step S11 is described in detail with reference to the flowchart of FIG. 3.

In Step S11, medical images for a test are selected from the medical images in the tests included in the case.

In Step S112, an area of a target organ is extracted from the images selected in Step S111. In this embodiment, an area of a liver is extracted. As an example of a liver area extracting approach, the following approach can be used: Non-patent Literature 2: "Improvement of an extraction method of liver regions based on gray pattern of abnormal regions (2nd Report)", Tanaka, Shimizu, and Kobatake, The Technical Report of IEICE, Medical Image, 104 (580), pp. 7-12, January 2005.

In Step S113, a lesion area is extracted from the organ area extracted in Step S112. In this embodiment, a tumor portion of the liver area is extracted. As an example of a liver tumor portion extracting approach, the following approach can be used: Non-patent Literature 3: "Development of an automated extraction method for liver tumors in three dimensional abdominal CT images (2nd Report)", Nakagawa, Shimizu, Hitosugi, and Kobatake, The Technical Report of IEICE, Medical Image, 102 (575), pp. 89-94, January 2003.

In Step S114, one of the lesion areas extracted in Step S113 is selected.

In Step S115, an image feature quantity is extracted from the lesion area selected in Step S114, In this embodiment, several image feature quantities applicable to a liver tumor are selected for use from four hundreds and ninety kinds of feature quantities described as image feature quantities in Non-patent Literature 1.

In Step S116, a check is made to detect whether or not any unselected lesion area remains among the lesion areas extracted in Step S113. When an unselected lesion area remains, a return is made to Step S114 and the unselected lesion area is selected and then Step S115 is executed again. When no unselected lesion remains, in other words, when all of the lesion areas extracted in Step S113 have already been subjected to feature quantity extraction in Step S115, a transition to Step S117 is made.

In Step S117, a check is made to detect whether or not any unselected medical image in the test remains in the case. When one or more unselected medical images remain, a return is made to Step S111 and the unselected medical images are selected one-by-one and then Steps S112 to Step S116 are executed on each of the unselected medical images. When no unselected medical images remains, in other words, when all of the lesion areas have already been subjected to feature quantity extraction in Step S115, the processing in the flowchart of FIG. 3 is terminated, and a return to the processing in the flowchart of FIG. 2 is made.

Figure 2:
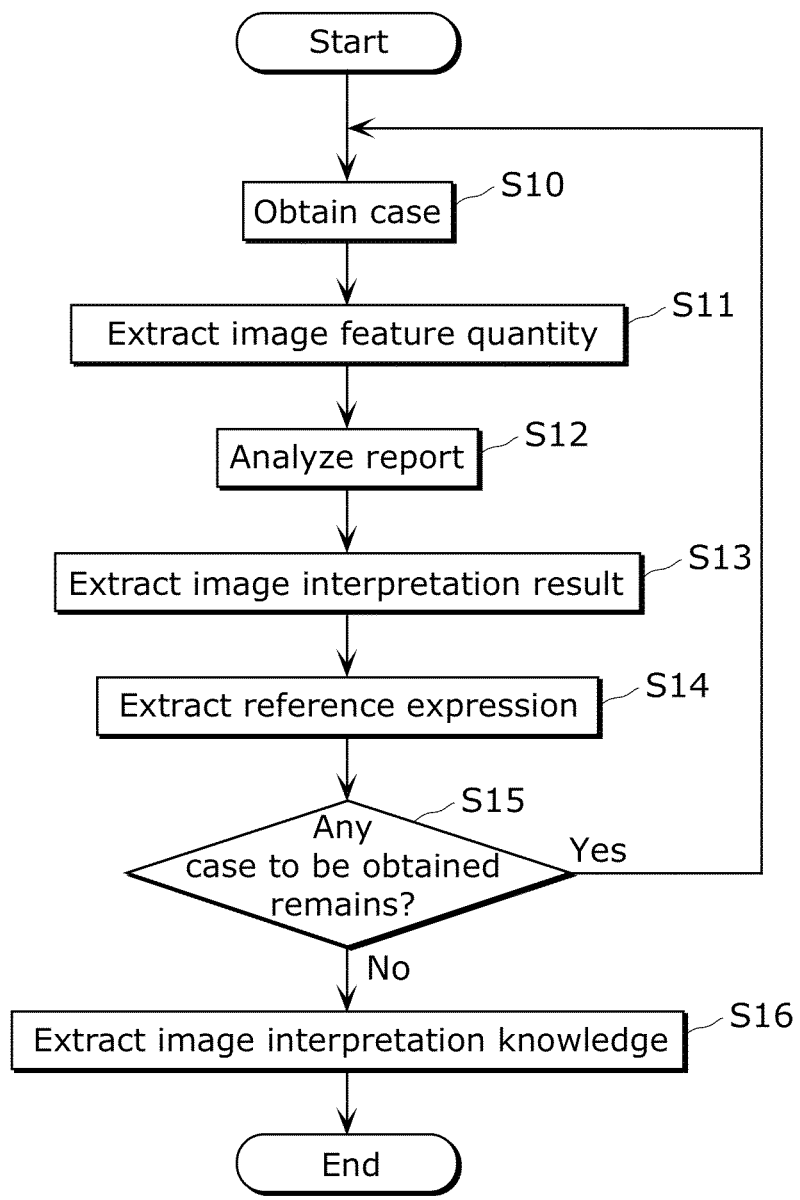
FIG. 2 is a flowchart of a procedure for generating image interpretation knowledge according to the embodiment.
Figures 3, 4:
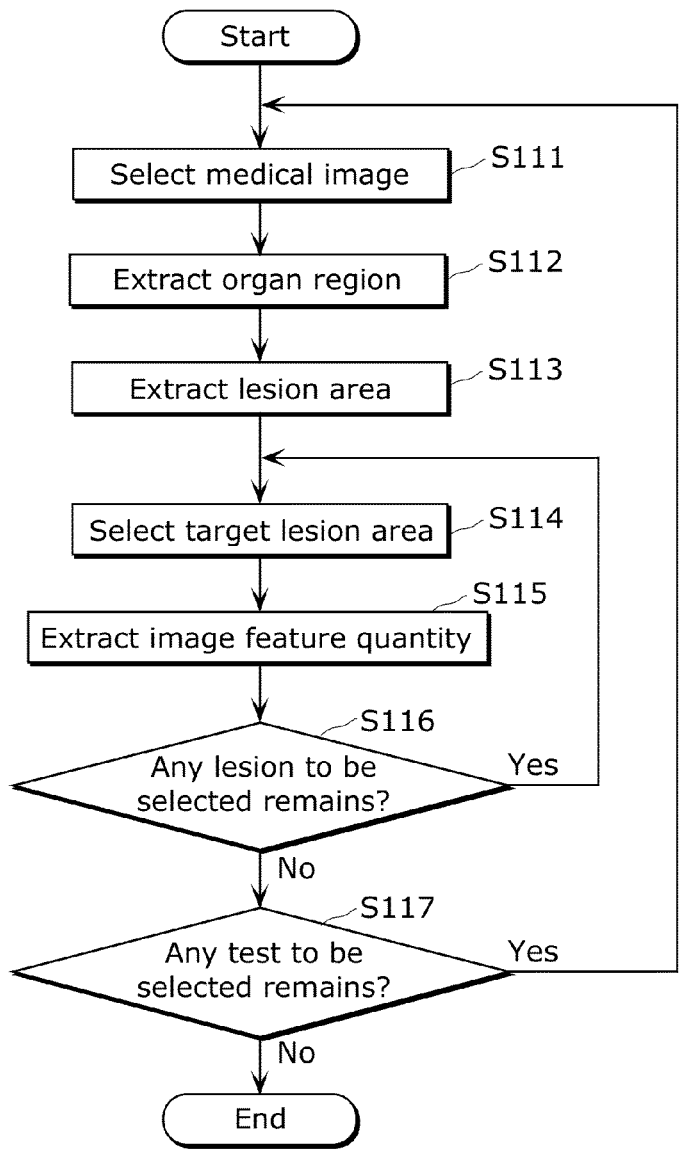
FIG. 3 is a flowchart of a procedure for extracting image feature quantities according to the embodiment.
FIG. 4 is a diagram showing an example of an image interpretation report regarding an abdominal CT scan according to the embodiment.

In Step S12 of FIG. 2, a process for analyzing an image interpretation report is performed. More specifically, the descriptions in the image interpretation report are divided into the descriptions of the current interpretation target image and the descriptions of the other test images. The descriptions obtained in the other tests are further divided on a test-by-test basis. In this embodiment, a morpheme analysis and a syntax analysis are made using a word dictionary including words corresponding to modality names and time-series changes. Examples of morpheme analysis techniques include Non-patent Literatures 4 and 5: MeCab (http://mecab.sourceforge.net) and ChaSen (http://chasen-legacy.sourceforge.jp), and examples of syntax analysis techniques include Non-patent Literatures 6 and 7: KNP (http://nlp.Kuee.kyoto-u.ac.jp/nl-resource/knp.html), CaboCha (http://chasen.org/~taku/software/cabocha/). Image interpretation reports are often written by doctors using expressions unique to image interpretation reports. Thus, for example, the following are developed: morpheme analysis techniques, syntax analysis techniques, and various word dictionaries exclusive for image interpretation reports. When a word corresponding to a modality name or a time-series change appears in a sentence, the report is divided. With these processes, the image interpretation report is divided on a per corresponding test basis. For example, in the case where a CT image interpretation report includes "in an MR" or "in a past test", the report is divided into descriptions related to the MR and past descriptions related to the CT.

In Step S13, image interpretation items and a disease name are extracted from the descriptions related to the current interpretation target image obtained in Step S12. In this embodiment, a morpheme analysis and a syntax analysis are made using an image interpretation item word dictionary storing image interpretation items related to the modality used to capture the interpretation target image and a disease name word dictionary storing disease names. Through these processes, words matching the words stored in the respective word dictionaries are extracted.

In Step S14, reference expressions are extracted from the descriptions of the other tests obtained in Step S12. In this embodiment, words are extracted using a modality-exclusive image interpretation item word dictionary storing image interpretation items according to the modality. Each of the extracted words is assigned with a modality name such as an "MR" apparatus and a "US" apparatus and an attribute indicating a time-series change such as "past". These modality name and attribute are determined as reference expressions. Hereinafter, reference expressions are represented in the form of "Attribute—Image interpretation item", for example, as "MR-T2 high signal".

Here, the results obtained through Step S13 and Step S14 are independent of each other, and thus the execution order may be reversed.

FIG. 4 is an example of an image interpretation report of an abdominal CT scan. FIGS. 5A, 5B, and 5C respectively show image interpretation items, a reference expression, and a disease name extracted from the image interpretation report in FIG. 4. Normally, several image interpretation items and no or several reference expressions are extracted while one disease name is extracted.

In addition, although only the words related to the image interpretation items and disease name are respectively extracted in FIGS. 5A and 5C, it is also possible to extract character strings indicating the locations of lesions in the image interpretation report and character strings indicating time phases at the same time. Here, supplemental information regarding the time phases is provided. It is considered that a contrast radiography for time-series image capturing using a rapid intravenous injection is useful for identifying a lesion in a liver. In a contrast radiography of a liver, images of the liver are generally captured in the following time phases: an arterial phase in which a contrast medium is infused into a liver artery and a stain of a polycythemia tumor is observed; a portal venous phase in which the contrast medium distributed in an intestinal tract and a spleen is infused from a portal vein to the liver, and a hepatocyte has a highest contrast; an equilibrium phase in which the contrast medium inside and outside the blood vessels of the liver reaches its equilibrium; and a late phase in which the contrast medium stays in a stroma of the liver. Image interpretation reports often include descriptions of information about the locations of lesions in organs, and information about time phases focused in contrast radiography. For this reason, the information about the locations and the information about the time phases extracted together with the image interpretation items are effective in the extraction of necessary information from the image interpretation knowledge described later. FIG. 6 shows an example where the information about locations and the information about time phases are extracted together with image interpretation items. For example, in the case of an analysis of an image interpretation report in FIG. 4, from a sentence clause that "Early stain is observed in liver segment S3", the "Liver segment S3" is extracted as a location attribute of the "Early stain". Likewise, from a sentence clause that "In late phase, equal absorption with hepatic mesenchymal is observed, resulting in unclearness.", the "Later phase" is extracted as a time phase attribute of the "Equal absorption".

When the image interpretation report in FIG. 4 is simply interpreted, the column for the time phase related to the "Early stain" and the column for the location related to the "Equal absorption" are blanks in the table of FIG. 6. On the other hand, when it is possible to utilize prepared knowledge that the image interpretation item "Early stain" is a term related to the early phase and to perform a context analysis that the tumor indicating the state of the "Early stain" refers to the tumor that shows "Equal absorption" in the "Late phase", the information about the location and the time phase attribute extracted in this case are as shown in FIG. 7. This operations are effective not only for image interpretation items but also for reference expressions.

The results obtained through Step S11 and Steps S12 to S14 are independent of each other, and thus the execution order may be reversed.

In Step S15, a check is made to detect whether or not any case to be obtained remains in the database storing cases for obtaining image interpretation knowledge. When a case to be obtained remains, a return is made to Step S10, the case is obtained, and Steps S11 to S14 are executed. When no case to be obtained remains, in other words, when all the cases have already been subjected to an image feature extraction process (Step S11), a report analysis process (Step S12), an image interpretation item extraction process (Step S13), and a reference expression extraction process (Step S14), a transition to Step S16 is made.

When Step S16 is reached, the following have been obtained for all of the cases: the image feature quantities extracted from all the test images and sets of image interpretation items, reference expressions, and disease names extracted from the image interpretation report.

In Step S16, image interpretation knowledge is extracted from the image feature quantities obtained in Step S11 and the image interpretation items, the disease name obtained in Step S13, and the reference expressions obtained in Step S14. In this embodiment, the image interpretation knowledge is the correlation between two of the three data types of the image feature quantity, the image interpretation item, and the disease name and the correlation between two of the three data types of the image feature quantity, the reference expression, and the disease name.

(1) Correlations Between Image Feature Quantities and Image Interpretation Items A description is given of how to calculate the correlation between the image feature quantity and the image interpretation item in each pair. A correlation ratio is used here from among several kinds of representation forms of correlations. A correlation used here is an index indicating the correlation between a qualitative data item and a quantitative data item, and is presented in Expression 1.

[Math. 1]

$$\eta^2 = \frac{\sum_i N_i (\bar{x}_i - \bar{x})^2}{\sum_i \sum_j (x_{ij} - \bar{x})^2} = \frac{S_B}{S_T} \quad \text{(Expression 1)}$$

Here, $x_{ij}$ denotes an i-th observed value that belongs to a category i of the qualitative data, $\bar{x}_i$ denotes the average value of observed values that belong to the category i of the qualitative data, $\bar{x}$ denotes the overall average value, $N_i$ denotes the number of observations that belong to the category i, $S_B$ denotes an inter-category dispersion, and $S_T$ denotes a total dispersion.

Image interpretation reports are classified into two categories based on the presence/absence of a certain image interpretation item, and these categories are assumed to be qualitative data items. The raw values of image feature quantities of a kind extracted from the medical images are assumed to be qualitative data items. For example, for each of the cases included in the case database for extracting image interpretation knowledge, the image interpretation reports are classified into the categories one of which includes image interpretation reports which include the certain image interpretation item and the other includes image interpretation reports which do not include the certain image interpretation item. Here, a description is given of an approach for calculating the correlation ratio between the image interpretation item "Early stain" and the image feature quantity "Average luminance value inside tumor in early phase", In Expression 1, it is assumed that the category i=1 includes the "Early stain", and that the category i=2 does not include the "Early stain". Here, $x_{1j}$ denotes the i-th observed value that is the "Average luminance value inside tumor in early phase" in the tumor image extracted from the case whose image interpretation report(s) include(s) the "Early stain". Here, $x_{2j}$ denotes the j-th observed value that is the "Average luminance value inside tumor in early phase" in the tumor image extracted from the case whose image interpretation report(s) do(es) not include the "Early stain". The "early stain" indicates that a CT value increases in the early phase in the contrast radiography, and thus the correlation ratio is expected to be increased (to a value close to 1) in this case. Furthermore, the early stain depends on the type of the tumor, but does not depend on the size of the tumor, and thus the correlation between the image interpretation item "Early stain" and an image feature quantity "Tumor size" is small (a value close to 0). In this way, the correlation between each of all the image interpretation items and each of all the image feature quantities are calculated.

Figure 8:
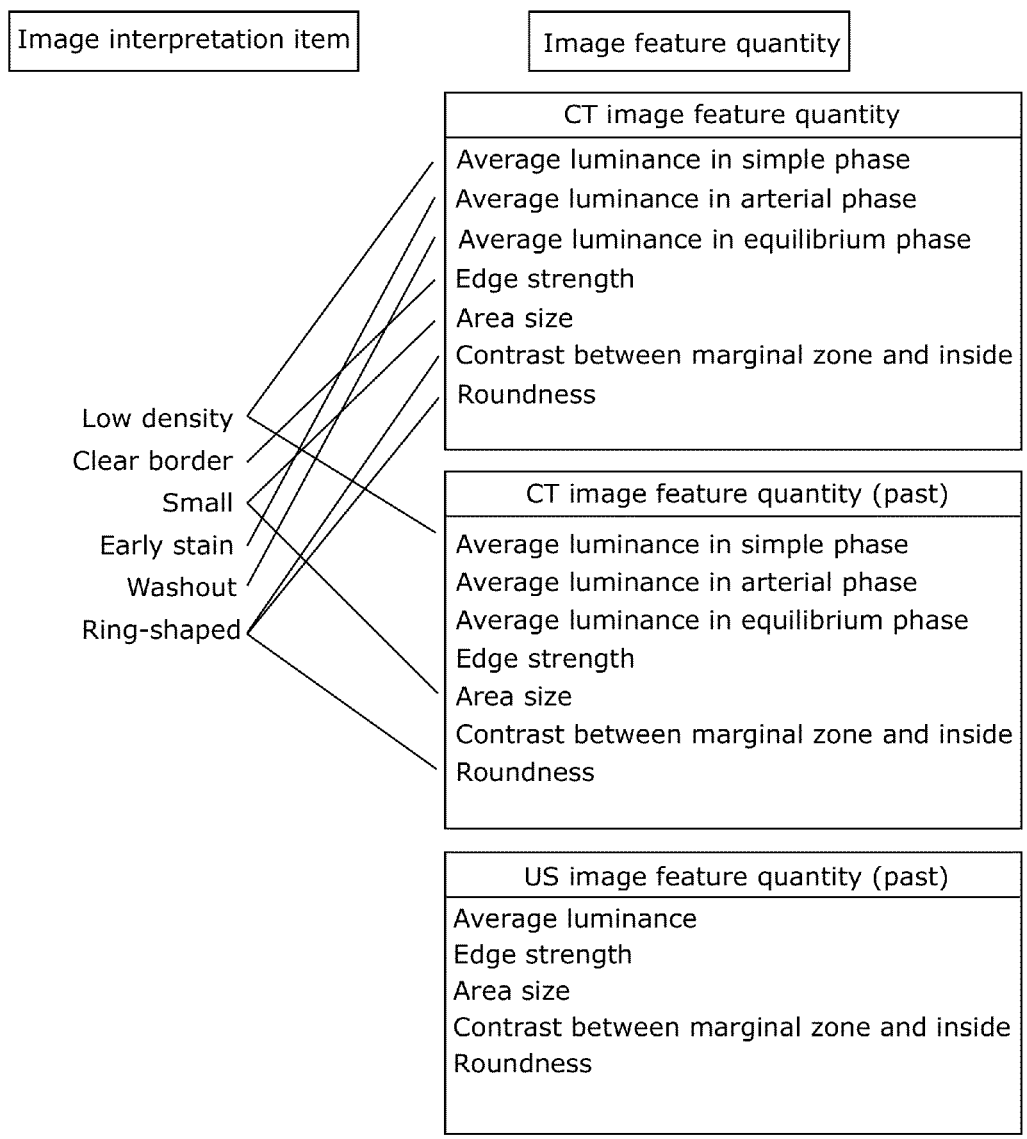
FIG. 8 is a conceptual chart of correlations (in a two-value representation) between image interpretation items and image feature quantities according to the embodiment.

FIG. 8 is a conceptual chart of correlations (here, correlation ratios) between image interpretation items and image feature quantities. The image interpretation items are listed at the left side, and the names of the image feature quantities are listed at the right side. Each of pairs of an image interpretation item and an image feature quantity having a correlation ratio larger than or equal to a threshold value is connected by a solid line. When the calculated correlation ratios are finally binarized based on the threshold value, information as shown in FIG. 8 is obtained. Supplemental information is given for this example. In contrast CT scans for detecting liver tumors, most tumors are drawn in a low density in CT images (that are called as simple images, simple CT images, simple phases, or the like) obtained before the application of contrast media. In most cases, the image interpretation reports of the tumors include any one of descriptions of "Low density", "Low Density Area (LDA) observed", and the like. For this reason, a high correlation is observed between the image interpretation items "Low density" and the average luminance value inside the tumors in the CT images before the application of the contrast media (an example of the average luminance value is shown as an abbreviated version that is "Average luminance in simple phase" in FIG. 8).

Figure 9:
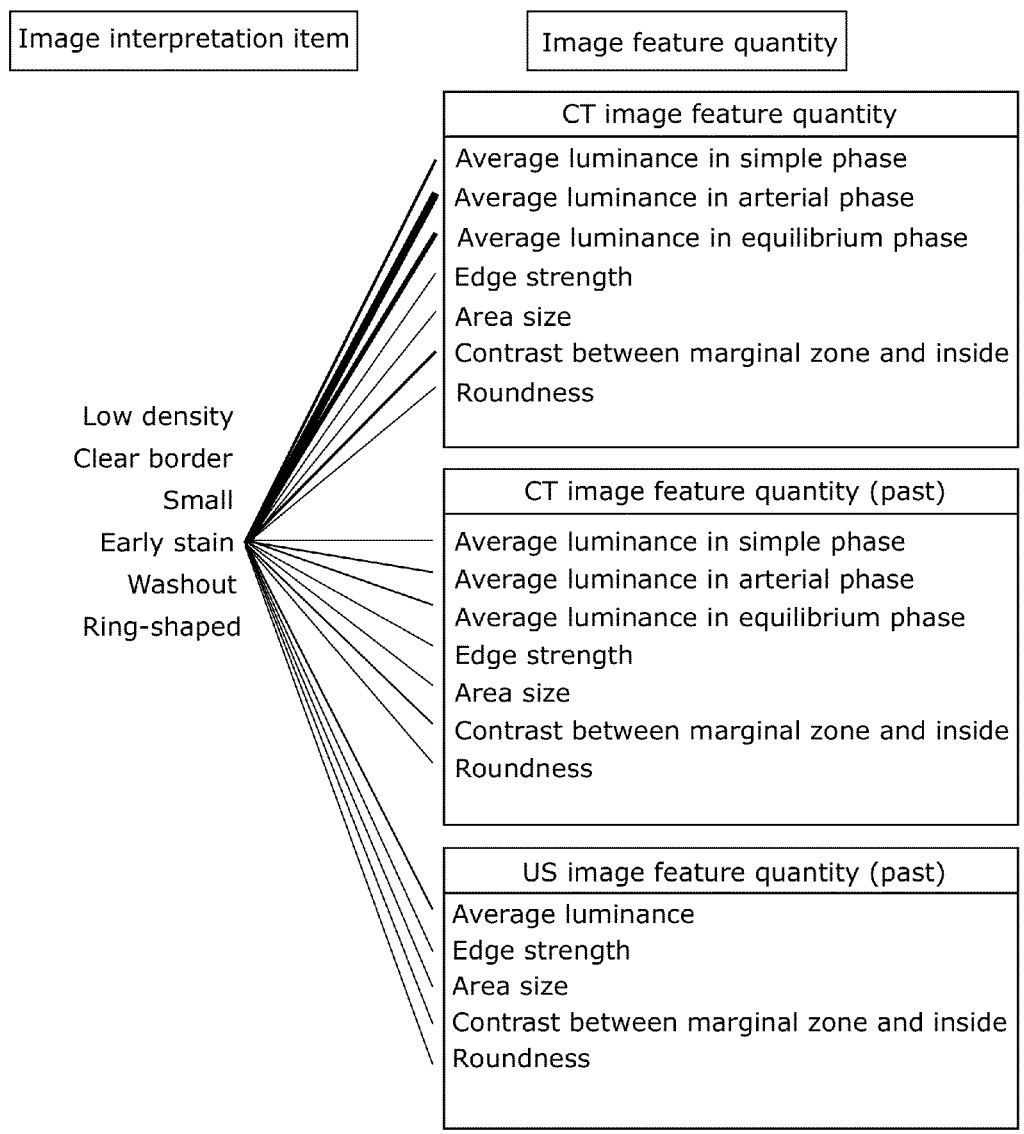
FIG. 9 is a conceptual chart of correlations (in a multi-value representation) between image interpretation items and image feature quantities according to the embodiment.

FIG. 9 is a conceptual chart of correlations (here, correlation ratios) between image interpretation items and image feature quantities. In this chart, the correlation ratios between the image interpretation items and the image feature quantities are shown in a multi-value representation in which the boldness of the solid lines corresponds to the magnitudes of the correlation ratios. For example, the highest correlation is observed between "Early stain" related to the early phase in which the CT value increases in the contrast radiography and the average luminance value inside the tumor (abbreviated as "Average luminance in arterial phase" in FIG. 9) in the early arterial phase (abbreviated as "Early phase" or "Arterial phase"). FIG. 9 shows the correlations between the image interpretation item "Early stain" and the respective image feature quantities. Likewise, there are correlation between each of the other image interpretation items and each of the image feature quantities.

Focusing on these values of the correlation ratios makes it possible to identify the image feature quantities highly related to the certain image interpretation item. In reality, it is highly likely that one case includes a plurality of lesions (tumors) and for which a plurality of images are captured. The image interpretation report of the case includes descriptions about the lesions. For example, in a contrast CT scan, CT images are captured at plural time points before and after the application of a contrast medium. For this reason, sets of slice images are obtained, each of the sets of slice images includes plural lesions (tumors), and a plurality of image feature quantities are extracted from each of the lesions. For this reason, image feature quantities are obtained in number that corresponds to the number obtained according to the Expression "(the number of sets of slice images)×(the number of lesions detected from a subject)×(the number of kinds of image feature quantities)". In addition, it is necessary to calculate the correlation between (i) each of the image feature quantities and (ii) each of the image interpretation items and the disease name extracted from the image interpretation report. There is a possibility that such correlations are calculated accurately by using a large number of cases. However, it is possible to calculate the correlations more accurately by associating, in advance, the descriptions in the image interpretation report and the image feature quantities corresponding to the descriptions to some extent based on, for example, the lesion locations and time phases as in FIG. 7.

In the above description, the image interpretation reports are classified into two categories based on the presence or absence of the certain image interpretation item. However, the image interpretation reports are classified into two categories based on the presence or absence of the certain image interpretation item (for example, "Clear border") and the antonym image interpretation item (for example, "Unclear border"). If the image interpretation items are presented in ordinal scales represented as descriptions "Low density", "Medium density", and "High density", it is possible to calculate the correlation ratios using these descriptions as categories (three categories in this example).

Furthermore, the synonyms such as "Low density", "Low luminance", and "Low absorption" are associated with each other as the identical image interpretation item in a synonym dictionary prepared in advance and handled as such.

((2) Correlations Between Image Feature Quantities and Reference Expressions

Figure 10:
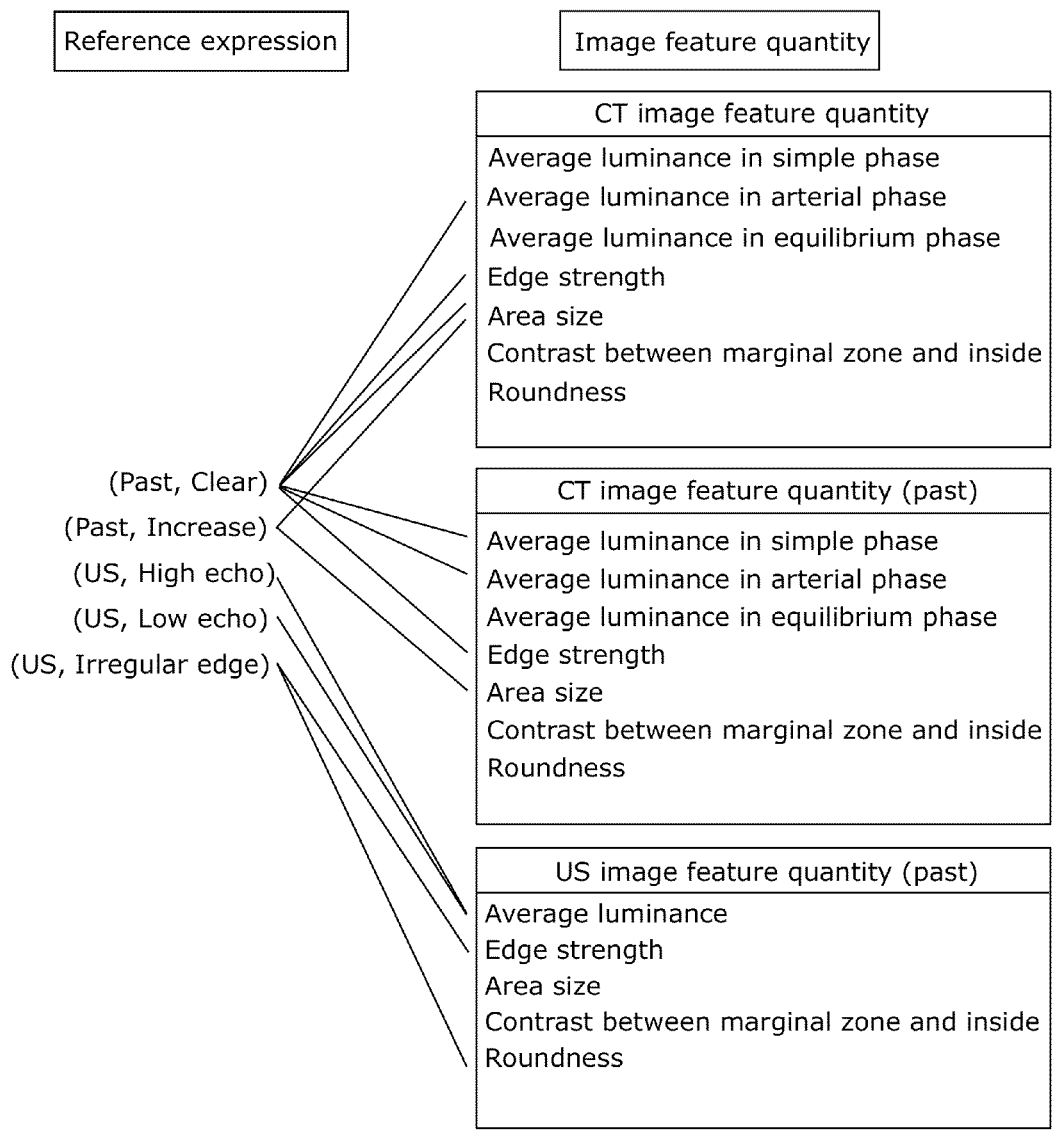
FIG. 10 is a conceptual chart of correlations (in a two-value representation) between reference expressions and image feature quantities according to the embodiment.

A correlation ratio can be used as the correlation between the image feature quantity and the reference expression in each pair, as in the example of the correlation between the image feature quantity and the image interpretation item in each pair. FIG. 10 is a conceptual chart of correlations (here, correlation ratios) between the reference expressions and the image feature quantities. Each reference expression is represented in the form of (a test name, an image interpretation item in the test). For example, in the case of a reference expression indicating a time-series change such as (Past, Increase), the reference expression has a high correlation with a feature of an area size of a current image, and has a high correlation with a feature of an area size of a past image captured by the same modality as the modality used to capture the current image. On the other hand, in the case of a reference expression indicating another test scheme such as (US, High echo), the reference expression has a high correlation with an image feature quantity corresponding to the target test, such as an average luminance of feature quantities in an image in the US. FIG. 10 shows correlations in a binary representation as in FIG. 8, but may show the correlations in a multi-value representation as in FIG. 9.

((3) Correlations Between Image Feature Quantities and Disease Names

Figure 11:
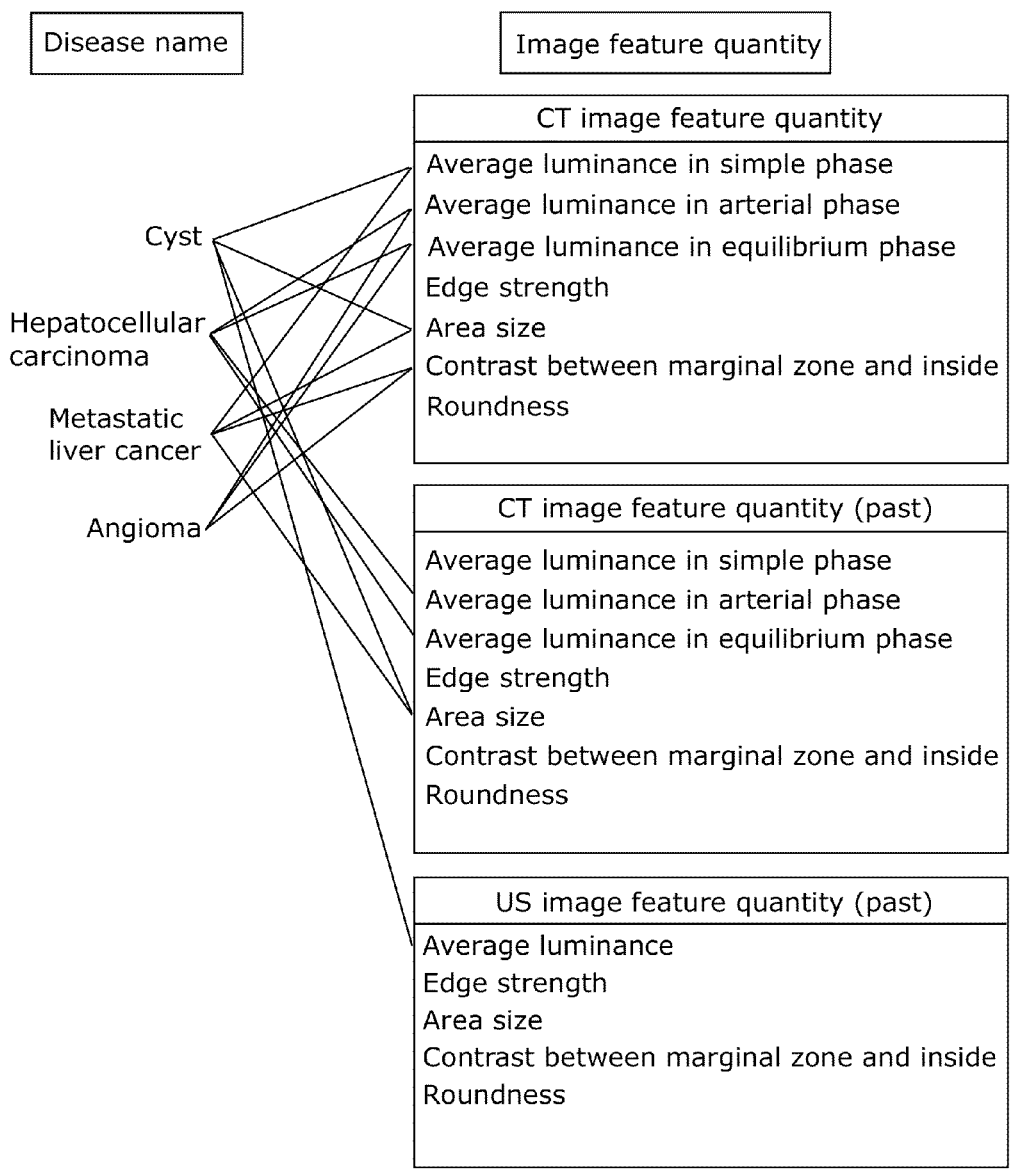
FIG. 11 is a conceptual chart of correlations (in a two-value representation) between disease names and image feature quantities according to the embodiment.

A correlation ratio can be used as the correlation between the image feature quantity and the disease name in each pair, as in the example of the correlation between the image feature quantity and the image interpretation item in each pair. FIG. 11 is a conceptual chart of correlations (here, correlation ratios) between the disease names and the image feature quantities. The correlations are shown in a binary representation as in FIG. 8, but it is possible to use a multi-value representation as in FIG. 9.

((4) Correlations between. Image Interpretation Items and Disease Names, and Correlations between Reference Expressions and Disease Names A description is given of how to calculate the correlation between the image feature quantity and the image interpretation item in each pair. A support value is used here from among several kinds of representation forms of correlations. A support value is an indicator indicating a correlation rule between qualitative data items, and is shown according to Expression 2.

[Math. 2]

$$\mathrm{support}(X \Rightarrow Y) = \frac{\mathrm{count}(X \cup Y)}{|D|} \quad \text{(Expression 2)}$$

Here, X and Y denote arbitrary item sets (X, Y ⊆ I),
|D| denotes the number of all transactions, and
count (X) is the number of transactions including the item set X in a database D.

Here, a correlation rule between the image interpretation item and the disease name in each pair is calculated. The definitions of the terms are modified as indicated below.

X denotes one image interpretation item,
X ⊆ $I_1$: $I_1$ denotes the item set related to an image interpretation item,
Y denotes one disease name,
Y ⊆ $I_2$: $I_2$ denotes the item set related to a disease name,

|D| denotes the number of all transactions, and count (X∪Y) is the number of cases whose image interpretation reports include both of the image interpretation item X and the disease name Y.

Each of these support values means the probability (co-occurrence probability) of the co-occurrence of the image interpretation item X and the disease name Y in each of the cases. The use of a support value makes it possible to identify a combination of a reference expression and a disease name having a high relationship (correlation).

It is to be noted that a confidence value according to Expression 3 or a lift value according to Expression 4 may be used instead of the support value.

[Math. 3]

$$\mathrm{confidence}(X \Rightarrow Y) = \frac{\mathrm{count}(X \cup Y)}{\mathrm{count}(X)} \quad \text{(Expression 3)}$$
$$= P(Y \mid X)$$

Here, X and Y are arbitrary item sets (X, Y ⊆ I), and
count (X) is the number of transactions including the item set X in the database D.

[Math. 4]

$$\mathrm{lift}(X \Rightarrow Y) = \frac{\mathrm{confidence}(X \Rightarrow Y)}{P(Y)} \quad \text{(Expression 4)}$$
$$= \frac{P(Y \mid X)}{P(Y)}$$

Here, X and Y are arbitrary item sets (X, Y ⊆ I),
count (X) is the number of transactions including the item set X in the database D,
P (Y) denotes the appearance probability of the item set Y, and $$P(Y) = \frac{\mathrm{count}(Y)}{|D|}$$

|D| denotes the number of all transactions.

Each of these confidence values means the probability of the appearance of the conclusion portion Y under the condition that the item of the condition portion X appears. When the disease name Y appears in any of the image interpretation reports in which the image interpretation item X appears, the image interpretation item X and the disease name Y are regarded as having a high correlation (correlation). Each of the lift values is an index showing how much the appearance probability (that is the confidence value) of the disease name Y under the condition that the image interpretation item X appears, with respect to the appearance probability of the disease name Y without the condition that the image interpretation item X appears. Alternatively, it is also possible to use conviction values and phi-coefficients. Conviction values and phi-coefficients are described in documents related to a correlation rule analysis. An example of such documents is Non-patent Literature 8: "Data Mining and its Applications", written by Kato Hamuro, and Yata, Asakura Publishing Co. Ltd.

The correlations between reference expressions and disease names can be calculated as in the case of the correlations between image interpretation items and the disease names.

Figure 12:
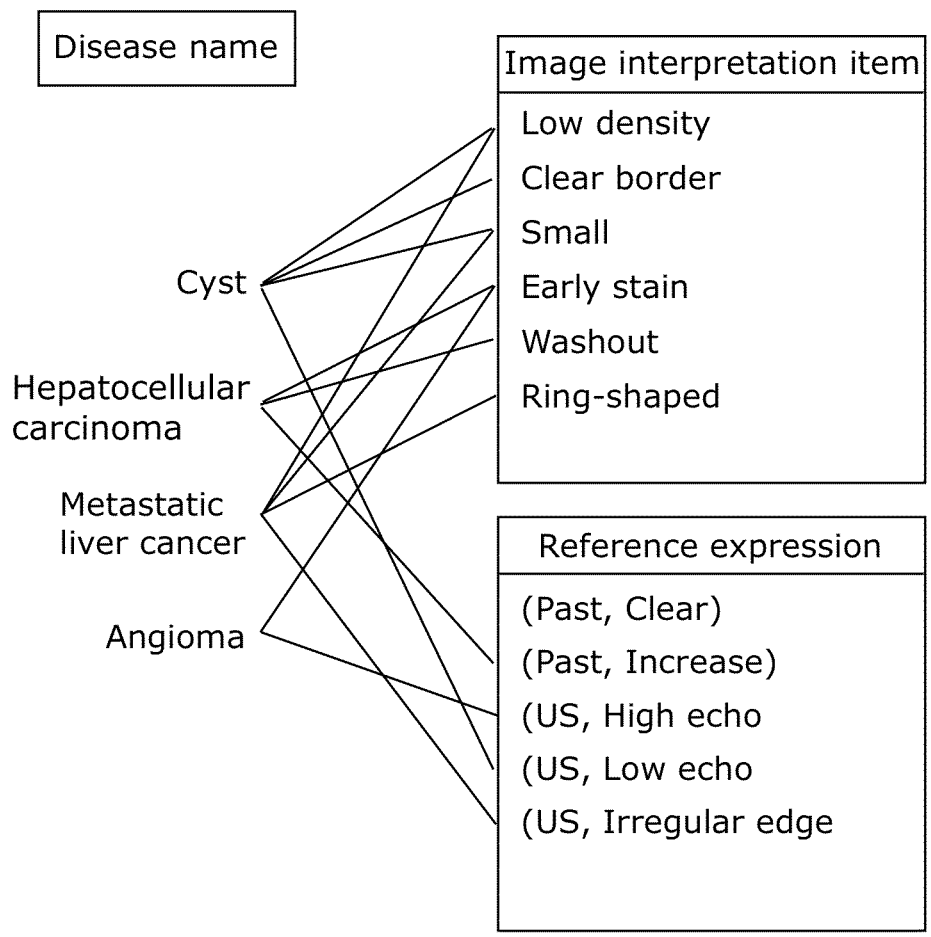
FIG. 12 is a conceptual chart of correlations (in a two-value representation) between image interpretation items and reference expressions according to the embodiment.

FIG. 12 shows a conceptual chart of correlations (for example, support values) between image interpretation items and disease names and correlations between reference expressions and the disease names at the same time. The correlations are shown in a binary representation as in FIG. 8, but it is naturally possible to use a multi-value representation as in FIG. 9.

When performing Step S16 according to the aforementioned approach, the following are respectively obtained: the correlations between image feature quantities and image interpretation items as in FIG. 13; the correlations between image feature quantities and disease names as in FIG. 14; the correlations between image interpretation items and disease names as in FIG. 15; the correlations between image feature quantities and reference expressions in the same form as in FIG. 13; and the correlations between reference expressions and disease names in the same form as in FIG. 15. Here, M denotes the total number of tests included in a case, and Test 1 is a test using an interpretation target image. Here, Test 1 corresponds to a CT. As for the other modalities, similar case searches are possible by generating tables as shown in FIGS. 13, 14, and 15. In addition, the obtained correlations are stored in the image interpretation knowledge database 110 in the forms of FIG. 13, FIG. 14 and FIG. 15.

(Similar Case Search)

Figure 16:
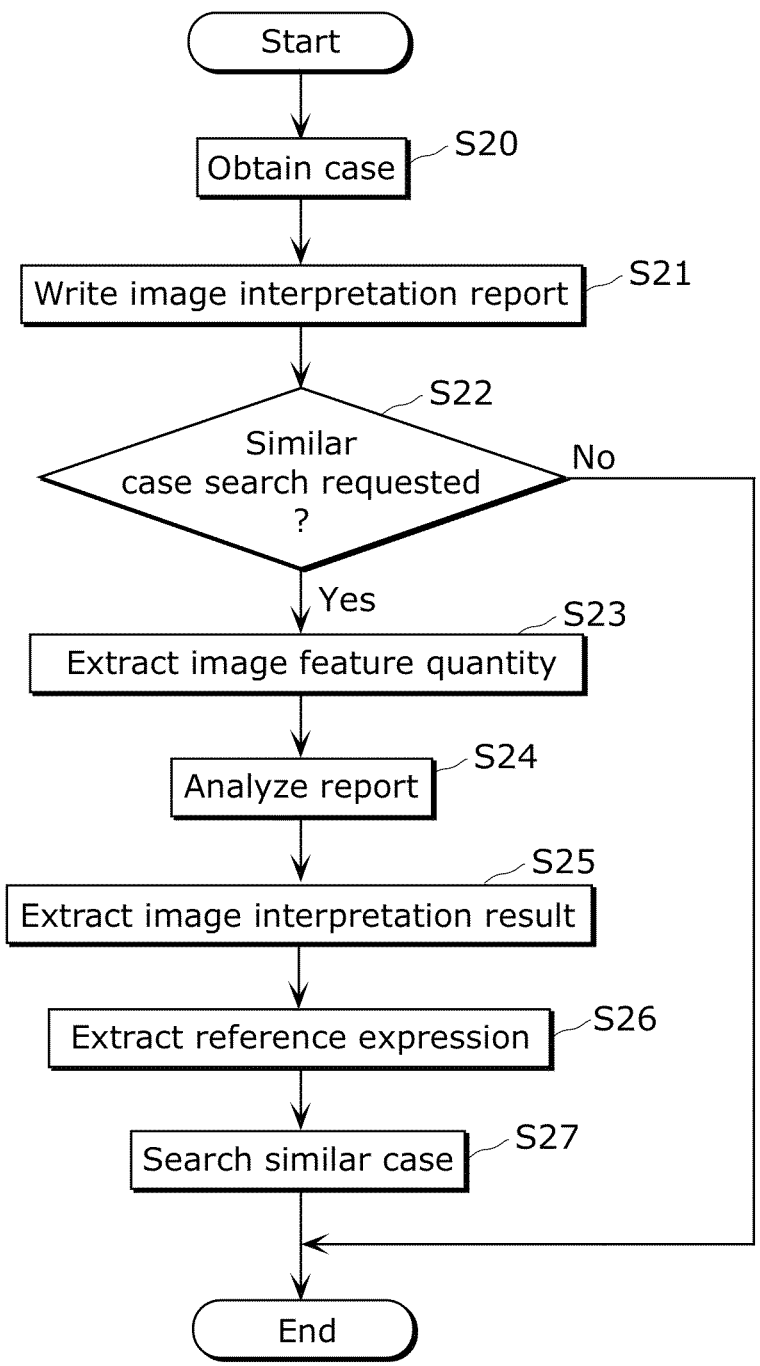
FIG. 16 is a flowchart of a procedure for searching a similar case according to the embodiment.
Figure 17:
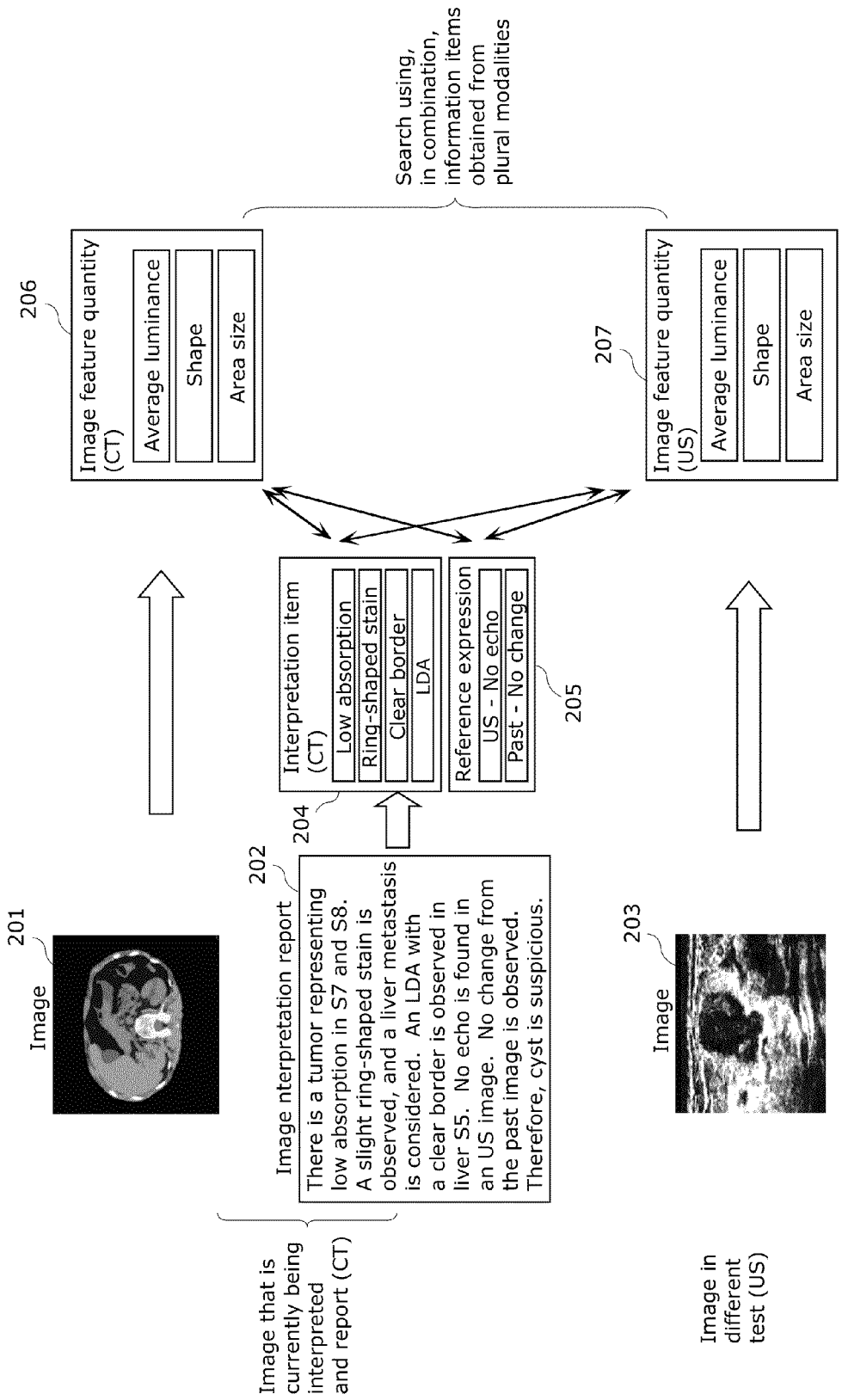
FIG. 17 is a diagram showing the outline of a similar case search according to the embodiment.

Hereinafter, a procedure of a similar case search is described using the flowchart of FIG. 16 and the diagram of FIG. 17 showing the outline of the similar case search.

In Step S20, the test image obtaining unit 120 obtains an interpretation target image from a medical image capturing apparatus. In addition, when there are one or more other test images (reference images) of the same subject, all of the test images are read. The test images may be directly specified or input by the image interpreter, or may be automatically obtained from a case database based on the ID of the subject. As in the generation of image interpretation knowledge in FIG. 2, the medical image capturing apparatus that is the target in this embodiment is a multi-slice CT apparatus, and the target organ and disease are the liver and a liver tumor. Each read image is displayed on the interpretation target image display unit 130. For example, in Step S20, an interpretation target image 201 and a test image 203 shown in FIG. 17 are obtained.

In Step S21, the user inputs the image interpretation report through the report input and output unit 140 with reference to the interpretation target image displayed on the interpretation target image display unit 130. In the case of the multi-slice CT apparatus, a plurality of slice images along a vertical surface (the axial view) with respect to the body axis is normally obtained through reconfiguration of the images. The user checks whether or not a lesion (a liver tumor in this embodiment) is present or absent while changing the slice locations on these slice images, and input descriptions in the image interpretation report. When inputting descriptions in the image interpretation report, the location (the slice number and the coordinate on the slice image or area information) of the lesion detected in the interpretation target image may be specified by the user using an input device such as a mouse. When a coordinate is specified, for example, an approximately center location of the tumor is clicked using a mouse. Examples of schemes to specify an area include, a scheme for enclosing a lesion area by a rectangle, a circle, or an oval circle, and a scheme for specifying a boundary between the lesion area and a normal organization using a free-form curve. The scheme for specifying only the center coordinate or specifying the area by enclosing the area by the rectangle, the circle, or the oval circle has an advantage of placing a small burden on the user, but requires that the tumor portion is automatically extracted from the area including the tumor using an image processing algorithm for an image feature quantity extraction. As for a tumor area extraction, the same approach as in Step S113 can be used. When the image interpreter does not specify the location of the lesion and the area, it is only necessary to perform a target organ area extraction in Step S112 and a lesion area extraction in Step S113. For example, in Step S21, an image interpretation report 202 shown in FIG. 17 is input.

In Step S22, a user's request for a similar case search is received.

In the case of a tumor having a typical symptom or a skilled doctor, inputs in the image interpretation report are normally completed without difficulty in the diagnosis. However, in the case of a tumor having a non-typical symptom or a fresh doctor, the doctor makes a request for a similar case search using the image interpreting terminal 220. When a plurality of lesions are present in the interpretation target image, one of the lesions which is difficult to diagnose is specified, and then such a request for a similar case search is performed.

How to specify these lesions is described next. When a plurality of locations or areas of the lesions including the lesion difficult to diagnose is already specified before inputs in the image interpretation report in Step S21, it is only necessary that one of these locations or areas is selected. When no lesion difficult to diagnose is yet specified in Step S21, one of the lesions is newly specified here. As the specification scheme, it is possible to specify one point around the center of the lesion, or to specify the lesion area. When the one point around the center is specified, a detailed lesion area is set using the same scheme as in Step S113 from the lesion area within a predetermined range with respect to the specified point. When the lesion area is roughly specified, the detailed lesion area is specified in the roughly-specified lesion area using the same scheme as in Step S113.

When such a doctor's request for a similar case search is made, a transition to Step S23 is made. At this time, input of descriptions in the image interpretation report may be completed, or may be in progress. The similar case search in Step S27 can be executed even when no descriptions is input in the image interpretation report. In this case, the similar case search is executed using a pre-set reference set of image features without executing any similar case search according to a doctor focus point although such similar case search is a feature of this embodiment.

When an image interpretation report input time lasts over a predetermined time or when an input for terminating the image interpretation report input time is made, the process in FIG. 16 is completed. The processing unit for receiving the similar case search request and the image interpretation termination input is not shown in FIG. 1. The processing unit may be a physical switch embedded in the keyboard or the like in the image interpreting terminal 220, or a GUI menu or the like displayed on the interpretation target image display unit 130 composed of a medical-use high-definition monitor or the like.

In Step £23, the image feature quantity extracting unit 180 extracts image feature quantities from each of the lesion areas specified or extracted in the interpretation target image in Step S22. When plural lesion areas are specified or extracted, all of a predefined number of feature quantities are extracted for each of the lesion areas. The scheme for extracting the image feature quantities is the same as in Step S115. At this time, image feature quantities in lesion areas corresponding to all of the other test images are also extracted at the same time. For example, in Step S23, the image feature quantity extracting unit 180 extracts an image feature quantity 206 from the interpretation target image 201 and extracts an image feature quantity 207 from the test image 203.

In Step S24, the report analyzing unit 150 analyzes the image interpretation report including the descriptions input in Step S21. Here, the same process as the process in Step S12 performed to generate the image interpretation knowledge database 110 is executed so as to divide the descriptions included in the image interpretation report into descriptions of an image that is currently being interpreted and descriptions of the other test images.

In Step S25, the image interpretation result extracting unit 160 performs processing similar to the processing performed in Step S13 so as to extract image interpretation items and a disease name from the descriptions of the currently being interpreted image obtained in the processing in Step S24. For example, the image interpretation result extracting unit 160 extracts an image interpretation item 204 shown in FIG. 17. Although no disease name is shown in FIG. 17, a disease name may be extracted.

In Step S26, the reference expression extracting unit 170 performs processing similar to the processing performed in Step S14 so as to extract reference expressions from each of the test images obtained in Step S24. For example, the reference expression extracting unit 170 extracts a reference expression 205 shown in FIG. 17.

The results obtained through Step S25 and Step S26 are independent of each other, and thus the execution order may be reversed.

In Step S27, the weight determining unit 190 and the similar case searching unit 200 search the case database 100 for similar cases based on the following: the image feature quantities of the interpretation target image extracted by the image feature quantity extracting unit 180, the image interpretation items and disease names extracted by the image interpretation result extracting unit 160, and the reference expressions extracted by the reference expression extracting unit 170. The searched-out similar cases are displayed on a similar case display unit 210. States considered here are as follows: the state in which the image interpretation report in FIG. 4 is already written by the doctor in Step S21; the state in which the image interpretation items, the disease name, and the reference expressions in FIGS. 5A to 5C are already extracted in Steps S25 and S26; and the sate in which the image feature quantities are already extracted from the interpretation target image in Step S23. In addition, the image interpretation knowledge database 110 already stores the correlations between two of three data types that are the image feature quantities, the image interpretation items, and the disease names and the correlations between two of three data types that are the image feature quantities, the reference expressions, and the disease names as shown in FIG. 13, FIG. 14, and FIG. 15.

In this embodiment, weighted distance calculations are performed in the similar case search, based on at least one of the image interpretation items, reference expressions, and disease name extracted from the image interpretation report. In other words, comparatively large weights are added to the image feature quantities related to the extracted at least one of the image interpretation items, reference expression, and disease name, and comparatively small weights are added to the image feature quantities not related to the same. In this way, it is possible to perform a similar case search reflecting the doctor focus points input in the image interpretation report. In other words, the similar case searching unit 200 calculates the weighted distances between the respective medical images stored in the case database 100 and the interpretation target image. The similar case searching unit 200 searches out, from the case database 100, the similar case that is a case including at least one medical image used to perform a weighted distance calculation that yields a value smaller than a predetermined threshold value. Alternatively, the similar case searching unit 200 searches out, from the case database 100, the similar case that is a case including medical images used to perform weighted distance calculations that yield a predetermined number of weighted distance values selected in the descending order of smallness.

For example, the weight determining unit 190 determines the weight for the image feature quantity 206 based on a value indicating the correlation between the image feature quantity 206 and one of the image interpretation item 204 and the reference expression 205 shown in FIG. 17. Likewise, the weight determining unit 190 determines the weight for the image feature quantity 207 based on a value indicating the correlation between the image feature quantity 207 and one of the image interpretation item 204 and the reference expression 205. A similar case is searched out by calculating weighted distances between the image feature quantities 206 and 207 and a plurality of image feature quantities extracted from medical images included in the case data registered in the case database 100.

Each of the weighted distances can be calculated, for example, according to Expression 5.

[Math. 5]

$$D_W(x, u^i) = \sqrt{\sum_{j=1}^{n} w_j(x_j - u^i_j)^2}$$ (Expression 5)

x denotes an unknown vector,
$u^i$ denotes an i-th vector among comparison targets,
n denotes the number of dimensions of a vector, and
$w_j$ denotes a weight on the j-th dimension.

Here, x denotes a vector to which all of the plurality of image feature quantities extracted from the interpretation target image are connected. In addition, $u^i$ denotes an image feature quantity extracted from the i-th case among the cases stored in the case database 100. When connecting different kinds of image feature quantities, canonicalization (normalization to average 0 and disperse 1) is performed in advance so as not to affect the difference in the scales of the feature quantities.

A specific example of a weight ng scheme is described below. In the weighting, the extracted image interpretation items and reference expressions are handled collectively and are not distinguished from each other. Hereinafter, an image interpretation item or/and a reference expression is represented as "an image interpretation item/a reference expression". A representation of "an image interpretation item/a reference expression" means "an image interpretation item or a reference expression" or "an image interpretation item and a reference expression".

(1) Case Where Both Image Interpretation Items and Disease Name Are Extracted from Image Interpretation Report This case corresponds to a state in which the doctor completes most of the inputs in the image interpretation report, and tries to confirm the inputs based on a result of a similar case search.

Here, descriptions are given of an example case of using the correlations between image interpretation items and image feature quantities and the correlations between reference expressions and the image feature quantities, and another example case of using the correlations between image interpretation items and disease names and the correlations between reference expressions and the disease names. The correlations between the aforementioned two types of information are used although the correlations between the disease names and the image feature quantities can also be used. This is because a doctor takes a thinking process of firstly determining image interpretation items that should be focused on in a medical image, and finally determining a disease name based on the results of making determinations on the image interpretation items.

At this time, from the image interpretation report in FIG. 4, "Early stain" is extracted as the image interpretation item as shown in FIG. 5A, "Equal absorption" is extracted as the reference expression as shown in FIG. 5B, and "Angioma" is extracted as the disease name as shown in FIG. 5C. The weight determining unit 190 obtains the correlation between "Early stain" and "Angioma", the correlation between "Equal absorption" and "Angioma", and the correlation between "MR-T2 high signal" and "Angioma", with reference to the correlation table of the correlations between image interpretation items and disease names and the correlations between reference expressions and the disease names stored in the form of FIG. 15 in the image interpretation knowledge database 110. Here, the raw numerical values indicating the obtained correlations are used as weights, and are respectively denoted as $w_x$, $w_y$, and $w_z$. In addition, the weight determining unit 190 obtains the correlation between each of the "Early stain", "Equal absorption", and "MR-T2 High signal" and each of all the image feature quantities, with reference to the correlation table of the correlations between image feature quantities and image interpretation items and the correlations between the image feature quantities and reference expressions stored in the form of the table of FIG. 13 in the image interpretation knowledge database 110. Here, the raw numerical values indicating the obtained correlations are used as weights, and are respectively denoted as $w_{a,i}$, $w_{b,i}$, and $w_{c,i}$. Here, i is a subscript showing the type of the image feature quantity. The weight determining unit 190 calculates the weight W corresponding to the i-th image feature quantity using these weights according to Expression 6.

[Math. 6]

$$W_i = w_x w_{a,i} + w_y w_{b,i} + w_z w_{c,i} \quad \text{(Expression 6)}$$

Figure 18:
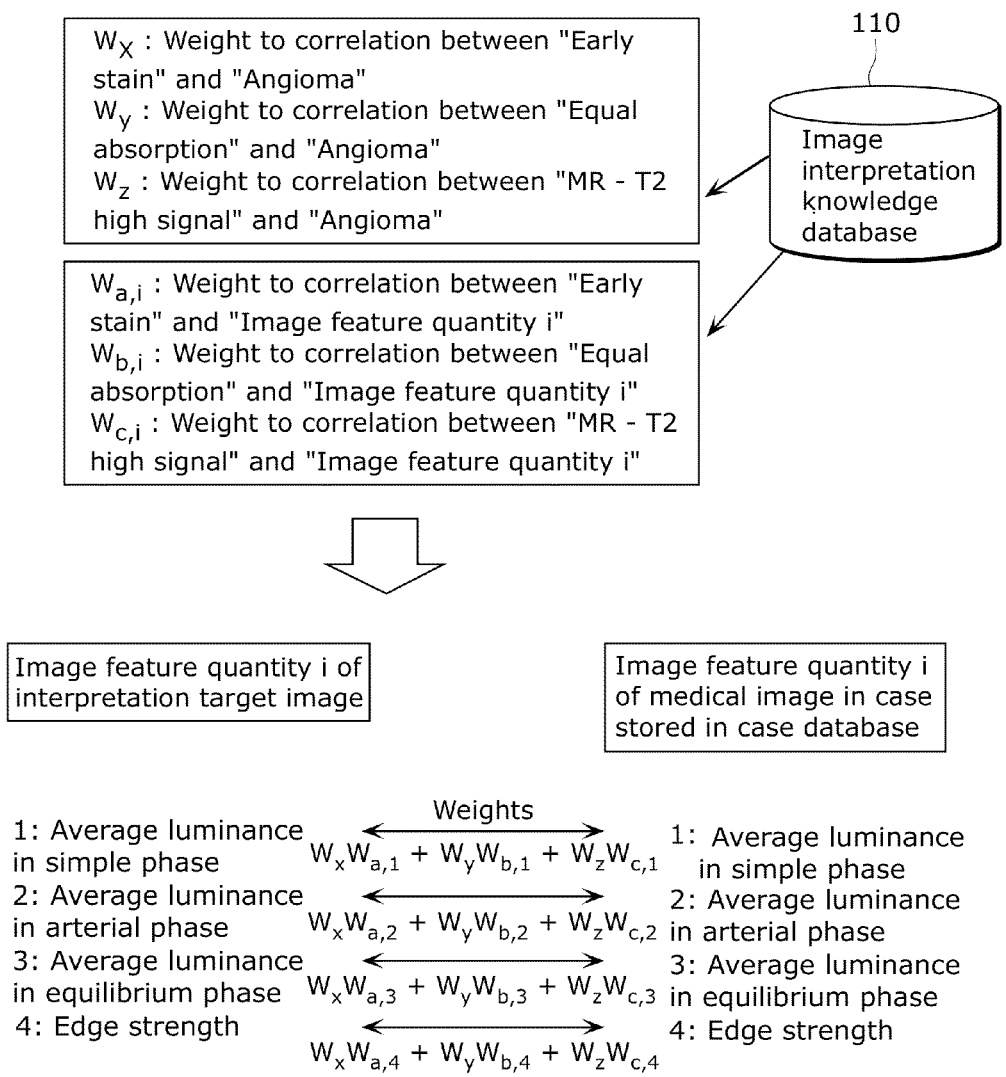
FIG. 18 is an illustration of a weighting scheme 1 in a search for a similar case according to the embodiment.

FIG. 18 shows the outline of the weighting scheme described above.

For example, the weight to a fourth image feature quantity "Edge strength" is calculated as a sum of $w_x w_{a,4}$, $w_y w_{b,4}$, and $w_z w_{c,4}$. Here, $w_x w_{a,4}$ is a value obtained by weighting the value $w_{a,4}$ indicating the correlation between Early stain and Edge strength using the value $w_x$ indicating the correlation between Early stain and Angioma related to the same image interpretation item. Here, $w_y w_{b,4}$ is a value obtained by weighting the value $W_{b,4}$ indicating the correlation between Equal absorption and Edge strength using the value $w_y$ indicating the correlation between Equal absorption and Angioma including the same image interpretation item. Here, $w_z w_{c,4}$ is a value obtained by weighting the value $w_{c,4}$ indicating the correlation between MR-T2 high signal and Edge strength using the value $w_z$ indicating the correlation between MR-T2 high signal and Angioma including the same reference expression.

In the case where the number of image interpretation items/reference expressions is a number other than 3, a weight can be calculated by adding (i) a value that indicates the correlation between an image interpretation item and an image feature quantity and is weighted using a value indicating the correlation between the image interpretation item and a disease name and (ii) a value indicating the correlation between a reference expression and the image feature quantity. According to this Expression, it is possible to calculate weights considering the image interpretation items/the reference expressions and the disease names focused by the doctor, the correlations between the image interpretation items/reference expressions and the disease names, and the correlations between the image feature quantities/reference expressions and image feature quantities. As a result, it is possible to perform a similar case search based heavily on the weighted information.

In the flowchart of FIG. 16, a similar case search is executed only when a similar case search request is made. However, it is also good to execute a similar case search at another timing during the input in the image interpretation report. An example of such another timing is employed in the case where no input is made in the image interpretation report over a certain time period after at least one image interpretation item/reference expression, or disease name is input. Assuming that the doctor has difficulty in interpreting the image, an operation approach is taken with an aim to accelerate the interpretation by presenting a similar case as a hint. In this embodiment, when the at least one image interpretation item/reference expression, or disease name is input, it is possible to execute a similar case search based on the doctor focus point. Hereinafter, descriptions are given of also a case where only the image interpretation item/reference expression is extracted from the image interpretation report and a case where only the disease name is extracted from the same.
((2) Case Where Only Image Interpretation Item/Reference Expression Can Be Extracted from Image Interpretation Report This case corresponds to a state in which the doctor can determine one or more image interpretation items that should be focused on to diagnose a disease, but has difficulty in making a final diagnosis of the disease, and thus is trying to get a hint for diagnosing the disease based on a result of a similar case search. Here, weighting is performed based only on the correlations between image interpretation items and image feature quantities and the correlations between reference expressions and the image feature quantities.

At this time point, it is assumed that the "Early stain" and "Equal absorption" are extracted as image interpretation items and "MR-T2 High signal" is extracted as a reference expression from the image interpretation report. The weight determining unit 190 obtains the correlation between each of the "Early stain", "Equal absorption", and "MR-T2 High signal" and each of all the image feature quantities, with reference to the correlation table of the correlations between the image feature quantities and the image interpretation items and the correlations between the image feature quantities and reference expressions stored in the form of the table of FIG. 13 in the image interpretation knowledge database 110. Here, the raw numerical values indicating the obtained correlations are used as weights, and are respectively denoted as $w_{a,i}$, $w_{b,i}$, and $w_{c,i}$. Here, i is a subscript showing the type of the image feature quantity. The weight determining unit 190 calculates the weight. W, corresponding to the i-th image feature quantity using these weights according to Expression 7.

[Math. 7]

$$W_i = w_{a,i} + w_{b,i} + w_{c,i} \quad \text{(Expression 7)}$$

Figure 19:
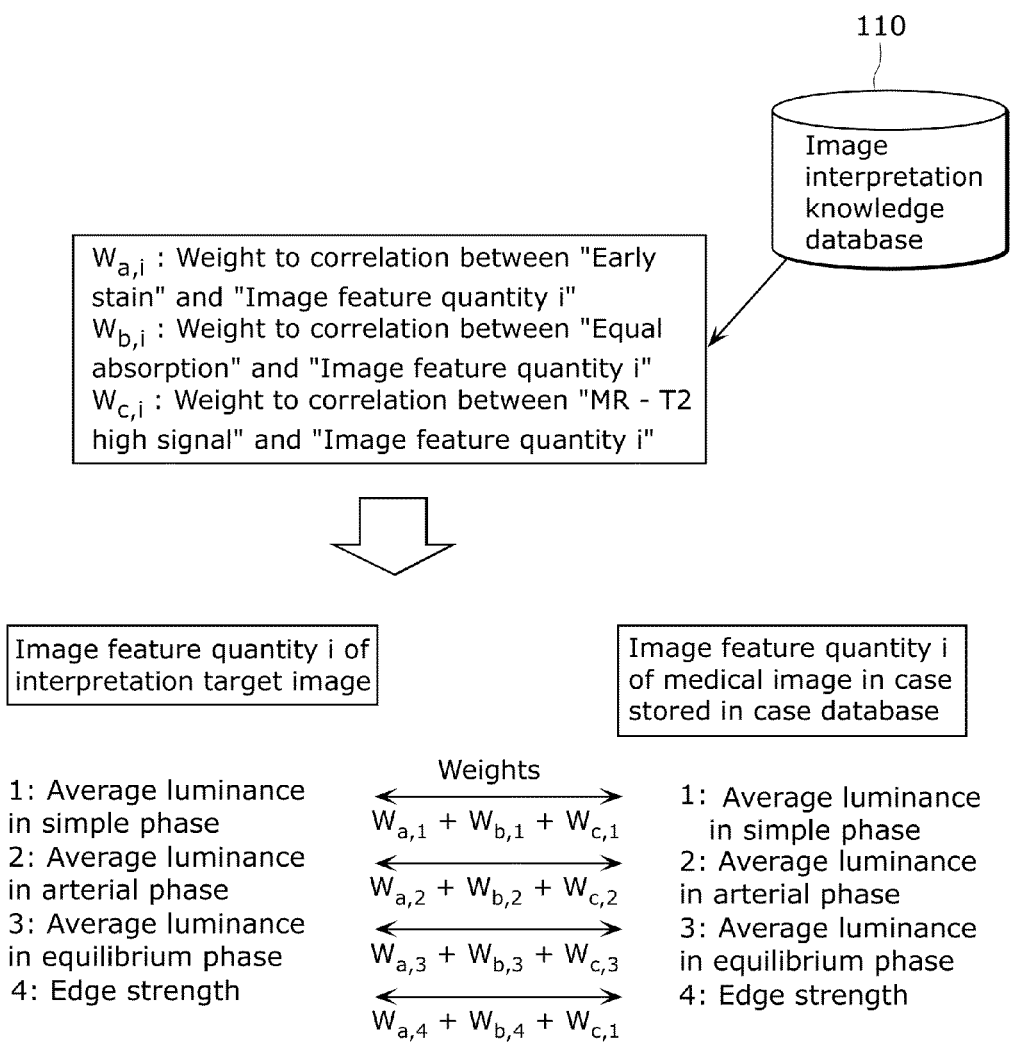
FIG. 19 is an illustration of a weighting scheme 2 in a search for a similar case according to the embodiment.

FIG. 19 shows the outline of the weighting scheme described above.

For example, the weight to the fourth image feature quantity "Edge strength" is a value obtained by adding the value $w_{a,4}$ indicating the correlation between Early stain and Edge strength, the value $w_{b,4}$ indicating the correlation between Equal absorption and Edge strength, and the value $w_{c,4}$ indicating the correlation between MR-T2 high signal and Edge strength.

When the number of the image interpretation items/reference expressions is other than 3, it is possible to calculate such a weight by adding the value indicating the correlation between the image interpretation item and the image feature quantity and the value indicating the correlation between the reference expression and the image feature quantity. According to this Expression, it is possible to calculate a weight considering the image interpretation item/reference expression focused by the doctor, and the correlation between the image interpretation item/reference expression and the image feature quantity. As a result, it is possible to perform a similar case search based heavily on the weighted information.

((3) Case Where Only Disease Name Can Be Extracted from Image Interpretation Report This case corresponds to a state in which the doctor can estimate the disease name based on his or her intuition and the like, but has difficulty in determining image interpretation items reference expressions that are the bases of the estimation, and thus is trying to get a hint for the bases (image interpretation items/reference expressions) of the diagnosis based on the result of the similar case search. Here, only on the correlations between the disease names and the image feature quantities are used.

At this time point, it is assumed that "Angioma" is extracted as the disease name in the image interpretation report. The weight determining unit 190 obtains the correlations between "Angioma" and the respective image feature quantities with reference to the correlation table between the image feature quantities and the disease names stored in the form of the table of FIG. 14 in the image interpretation knowledge database 110. Here, the raw numerical values indicating the correlations are used as weights, and are denoted as $w_i$. Here, i is a subscript showing the type of the image feature quantity. The weight determining unit 190 calculates the weight $W_i$ corresponding to the i-th image feature quantity using these weights according to Expression 8.

[Math. 8]

$$W_i = w_i \quad \text{(Expression 8)}$$

Figure 20:
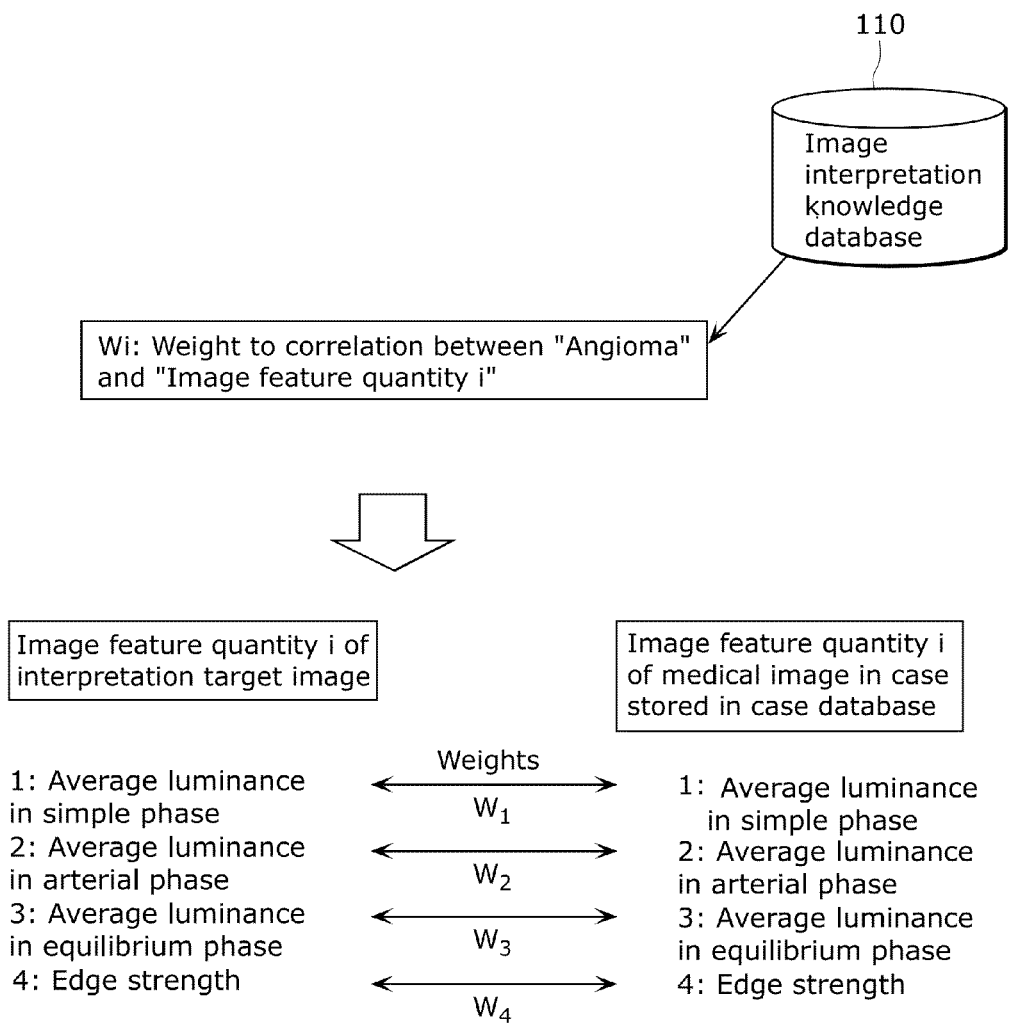
FIG. 20 is an illustration of a weighting scheme 3 in a search for a similar case according to the embodiment.

FIG. 20 shows the outline of the weighting scheme described above.

For example, the weight to the fourth image feature quantity "Edge strength" is the value $w_4$ indicating the correlation between Angioma and Edge strength The disease name is normally one, and thus it is only necessary to perform the aforementioned processes. However, when two or more disease names are input, it is only necessary to determine, as weights, the total sums of values indicating the correlations between the disease names and the image feature quantities. Adding the weights makes it possible to search for a similar case based on the averaged image feature quantity related to the two or more diseases. According to this Expression, it is possible to calculate the weights considering image interpretation items focused by the doctor, and the correlations between the image interpretation items and the image feature quantities. As a result, it is possible to perform a similar case search based heavily on the weighted information.

In this embodiment, a determination on the similarity between images is made using a weighted distance according to Expression 5. However, as the number of dimensions of feature quantities for use increases, some of feature quantities having a large correlation ratio may be embedded among a large number of feature quantities having a small (or a medium) correlation ratio in the calculated distances. In this case, it is also good to use, in distance calculations, only image feature quantities having a correlation ratio larger than or equal to a predetermined threshold value or only several image feature quantities having correlation ratios in a top range. The number of image feature quantities in such a case may be determined in advance.

In the similar case search according to this embodiment, weighted distance calculations are performed in the similar case search, based on at least one image interpretation item, reference expressions, and disease name extracted from the image interpretation report. In other words, comparatively large weights are added to the image feature quantities related to the extracted at least one image interpretation item, reference expression, and disease name, and comparatively small weights are added to the image feature quantities not related to the same. In this way, it is possible to perform a similar case search reflecting the doctor focus point input in the image interpretation report. In particular, the use of a reference expression makes it possible to perform weighting on an image feature quantity based on descriptions regarding the other tests of the same subject. In this way, it is possible to provide similar case searching apparatuses capable of performing similar case searches in which the user focus point is reflected and information obtained in the tests performed by different modalities or information of time-series changes is included.

Although the similar case searching apparatus according to this embodiment has been described above, the exemplary embodiment does not limit the inventive concept, the scope of which is defined in the appended Claims and their equivalents.

For example, in the above embodiment, the test image obtaining unit 120 obtains images in the other tests together with an interpretation target image. However, the test image obtaining unit 120 may obtain only the interpretation target image. In this case, a similar case search is executed using, as image feature quantities, only the image feature quantities extracted from the interpretation target image. Even in such a scheme, it is possible to provide advantageous effects similar to those obtained in the above embodiment.

Figure 21:
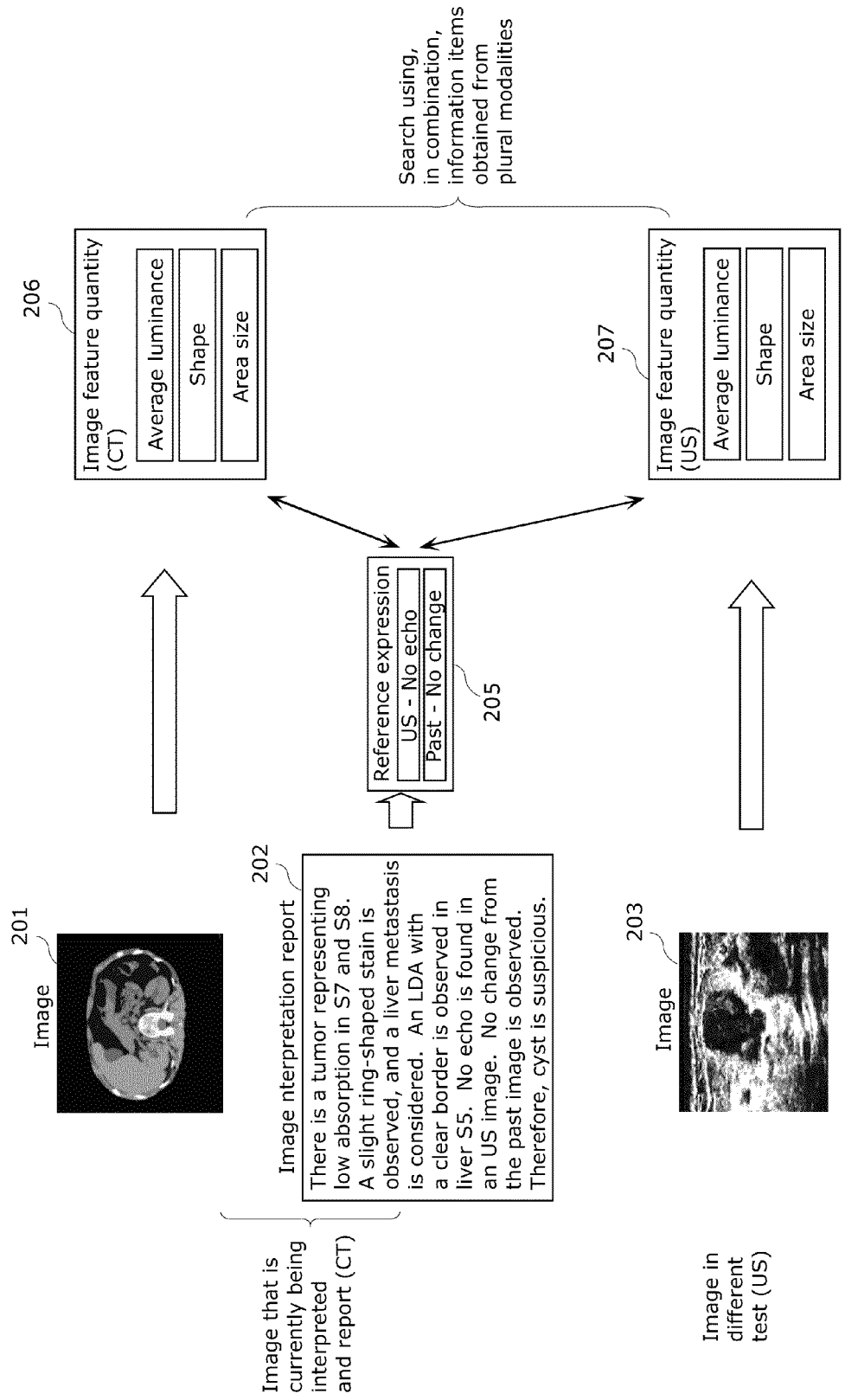
FIG. 21 is a diagram showing the outline of a similar case search according to the embodiment.

The similar case searching apparatus according to the embodiment performs weighting on the image feature quantities using both the image interpretation items and the reference expressions. However, as shown in FIG. 21, it is also good to perform weighting on image feature quantities using only reference expressions. In this case, the similar case searching apparatus does not always need to include an image interpretation result extracting unit 160. The weight determining unit 190 determines weights respectively added to the image feature quantities to be used for image search, based on the reference expressions extracted by the reference expression extracting unit 170, the image feature quantities extracted by the image feature quantity extracting unit 180, and the image interpretation knowledge stored in the image interpretation knowledge database 110. This weight determining scheme is the same as in the above embodiment except for not using any image interpretation items in the determination of the weights. For this reason, no detailed descriptions thereof is repeated. With this configuration, when an image interpretation report includes descriptions of not only an image that is currently being interpreted but also test images other than the current image, it is possible to perform a similar case search particularly focusing on the image feature quantities related to the descriptions of the test images.

Figure 22:
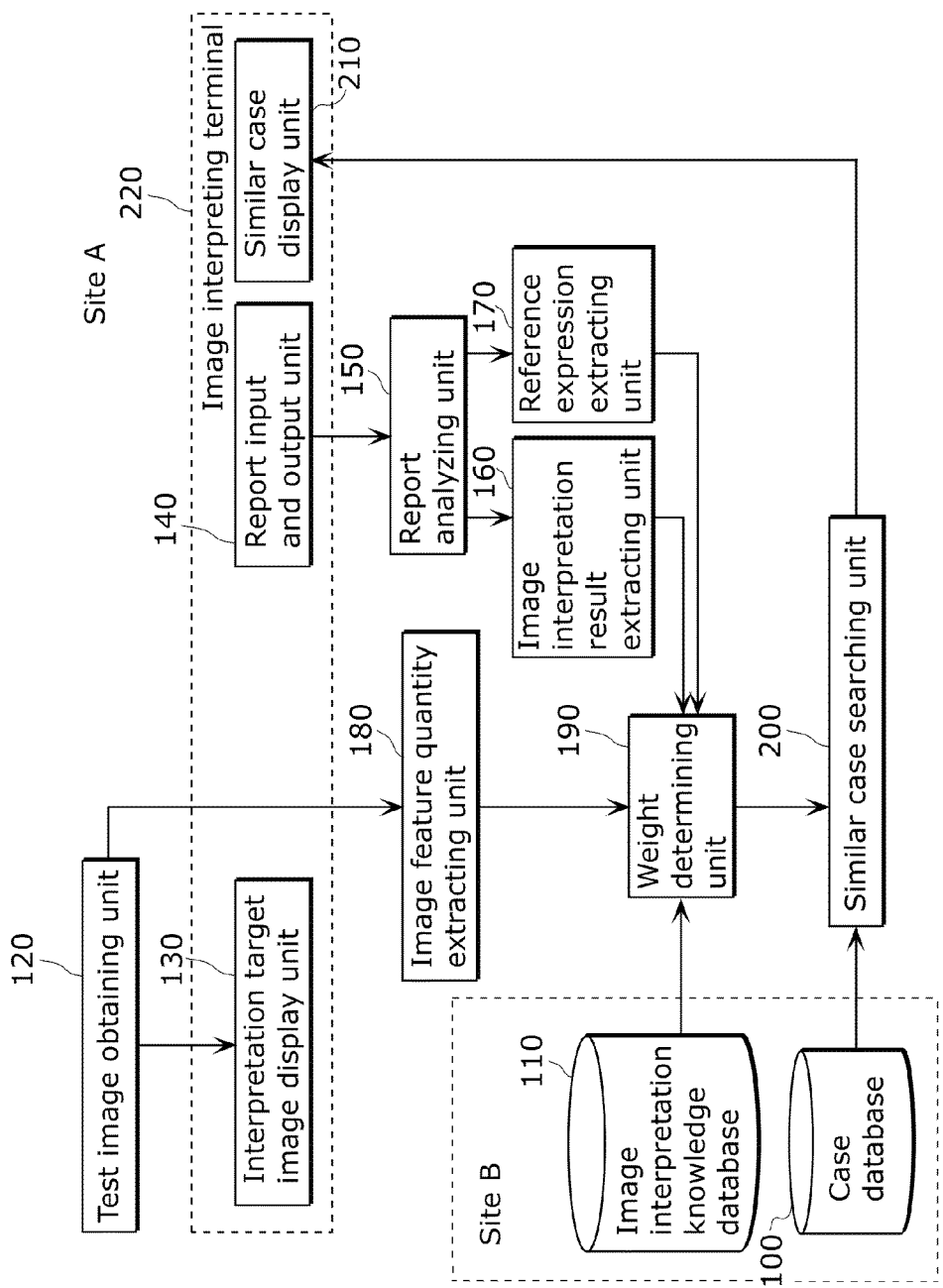
FIG. 22 is a block diagram of a structure of a similar case searching apparatus according to the embodiment.

In addition, as shown in FIG. 22, the similar case searching apparatus does not always need to include an image interpretation knowledge database 110 and a case database 100. In other words, these databases may be provided at Site B different from Site A in which the similar case searching apparatus is present. In this case, the weight determining unit 190 and the similar case searching unit 200 of the similar case searching apparatus are respectively connected to the image interpretation knowledge database 110 and the case database 100 via a network.

It is to be noted that the essential structural elements of the similar case searching apparatus are the image feature quantity extracting unit 180, the report analyzing unit 150, the reference expression extracting unit 170, the weight determining unit 190, and the similar case searching unit 200, and that the other structural elements are not always required to achieve the aim in the present disclosure.

In addition, each of the above apparatuses may be configured as, specifically, a computer system including a microprocessor, a ROM, a RAM, a hard disk unit, a display unit, a keyboard, a mouse, and so on A computer program is stored in the RAM or hard disk unit. The respective apparatuses achieve their functions through the microprocessor's operations according to the computer program. Here, the computer program is configured by combining plural instruction codes indicating instructions for the computer so as to allow execution of predetermined functions.

Furthermore, a part or all of the structural elements of the respective apparatuses may be configured with a single system-LSI (Large-Scale Integration). The system-LSI is a super-multi-function LSI manufactured by integrating constituent units on a single chip, and is specifically a computer system configured to include a microprocessor, a ROM, a RAM, and so on. A computer program is stored in the RAM. The system-LSI achieves its/their function(s) through the microprocessor's operations according to the computer program.

Furthermore, a part or all of the structural elements constituting the respective apparatuses may be configured as an IC card which can be attached to and detached from the respective apparatuses or as a stand-alone module. The IC card or the module is a computer system configured from a microprocessor, a ROM, a RAM, and so on. The IC card or the module may also be included in the aforementioned super-multi-function LSI. The IC card or the module achieves its/their function(s) through the microprocessor's operations according to the computer program. The IC card or the module may also be implemented to be tamper-resistant.

In addition, the respective apparatuses and their equivalents according to the present disclosure may be realized as methods including the steps corresponding to the unique units of the apparatuses. Furthermore, these methods according to the present disclosure may also be realized as computer programs for executing these methods or digital signals of the computer programs.

For example, the program causes a computer to search a case database for a similar case data item similar to a target case data item of a target case to be diagnosed, the case database storing a plurality of case data items, each of the case data items and the target case data item including one or more medical images and an image interpretation report that is a document data item indicating a result of interpreting the one or more medical images. More specifically, the program causes a computer to execute the following: extracting a plurality of image feature quantities from an interpretation target image which is a medical image and obtained by carrying out a first test on a subject; analyzing a target image interpretation report which is generated by a user in interpretation of the interpretation target image, and dividing descriptions in the target image interpretation report into a description related to the first test and a description related to a second test different from the first test carried out on the subject of the first test; extracting, from the description related to the second test, one or more reference expressions each of which is a character string indicating a feature of a medical image, each of the reference expressions indicating a feature of a reference image obtained by carrying out the second test on the subject of the first test; determining, for each of the image feature quantities extracted from the interpretation target image, a weight based on two-data correlation information that is prepared information defining a correlation between each of image feature quantities extracted from one or more medical images and each of one or more reference expressions extracted from an image interpretation report of the one or more medical images, the weight to the extracted image feature quantity having a value that is larger as the correlation between the image feature quantity and the reference expression extracted from the description related to the second test is higher; and searching the case database for the similar case data item including a similar image similar to the interpretation target image, by weighting each of the image feature quantities in a first set extracted from the interpretation target image and a corresponding one of the image feature quantities in a second set extracted from the one or more medical images included in the case data item registered in the case database, using the weight to each of the determined image feature quantities, and comparing the weighted image feature quantities in the first set and the weighted image feature quantities in the second set.

Such computer programs or digital signals according to the present disclosure may be recorded on computer-readable non-volatile recording media such as flexible discs, hard disks, CD-ROMs, MOs, DVDs, DVD-ROMs, DVD-RAMs, BDs (Blu-ray Disc (registered trademark)), and semiconductor memories. In addition, these methods according to the present disclosure may also be realized as the digital signals recorded on these non-volatile recording media.

Furthermore, these methods according to the present disclosure may also be realized as the aforementioned computer programs or digital signals transmitted via a telecommunication line, a wireless or wired communication line, a network represented by the Internet, a data broadcast, and so on.

The apparatuses (or computers or a computer system) according to the present disclosure may also be implemented as a computer system including a microprocessor and a memory, in which the memory stores the aforementioned computer program and the microprocessor operates according to the computer program.

Furthermore, it is also possible to execute another independent computer system by transmitting the programs or the digital signals recorded on the aforementioned non-transitory recording media, or by transmitting the programs or digital signals via the aforementioned network and the like.

Similar case searching apparatus according to one or more aspects of the present disclosure have been described based on the exemplary embodiment. However, the exemplary embodiment does not limit the inventive concept, the scope of which is defined in the appended Claims and their equivalents. Those skilled in the art will readily appreciate that various modifications may be made in the exemplary embodiment, and other embodiments may be made by arbitrarily combining some of the structural elements of different exemplary embodiments without materially departing from the principles and spirit of the inventive concept, the scope of which is defined in the appended Claims and their equivalents.

The herein disclosed subject matter is to be considered descriptive and illustrative only, and the appended Claims are of a scope intended to cover and encompass not only the particular embodiment disclosed, but also equivalent structures, methods, and/or uses.

INDUSTRIAL APPLICABILITY

The present disclosure is applicable to similar case searching apparatuses which search and present similar cases provided to users (such as doctors) for reference, image interpretation training apparatuses for fresh doctors, and the like.

The invention claimed is:

1. A similar case searching apparatus which searches a case database for a similar case data item similar to a target case data item of a target case to be diagnosed, the case database storing a plurality of case data items, each of the case data items and the target case data item including one or more medical images and an image interpretation report that is a document data item indicating a result of interpreting the one or more medical images, the similar case searching apparatus comprising:
    an image feature quantity extracting unit configured to extract a plurality of image feature quantities from an interpretation target image which is a medical image and obtained by carrying out a first test on a subject;
    a report analyzing unit configured to analyze a target image interpretation report which is generated by a user in interpretation of the interpretation target image, and divide descriptions in the target image interpretation report into a description related to the first test and a description related to a second test different from the first test carried out on the subject of the first test;
    a reference expression extracting unit configured to extract, from the description related to the second test divided by the report analyzing unit, one or more reference expressions each of which is a character string indicating a feature of a medical image, each of the reference expressions indicating a feature of a reference image obtained by carrying out the second test on the subject of the first test;
    a weight determining unit configured to determine, for each of the image feature quantities extracted from the interpretation target image by the image feature quantity extracting unit, a weight based on two-data correlation information that is prepared information defining a correlation between each of image feature quantities extracted from one or more medical images and each of one or more reference expressions extracted from an image interpretation report of the one or more medical images, the weight to the extracted image feature quantity having a value that is larger as the correlation between the image feature quantity and the reference expression is higher; and
    a similar case searching unit configured to search the case database for the similar case data item including a similar image similar to the interpretation target image, by weighting each of the image feature quantities in a first set extracted from the interpretation target image by the image feature quantity extracting unit and a corresponding one of the image feature quantities in a second set extracted from the one or more medical images included in the case data item registered in the case database, using the weight to each of the image feature quantities determined by the weight determining unit, and comparing the weighted image feature quantities in the first set and the weighted image feature quantities in the second set.

2. The similar case searching apparatus according to claim 1,
    wherein the report analyzing unit is configured to divide, as the description related to the second test, a description related to a medical image capturing apparatus different from a medical image capturing apparatus used in the first test, from the interpretation target report.

3. The similar case searching apparatus according to claim 1,
    wherein the report analyzing unit is configured to divide, as the description related to the second test, a description related to a test carried out in the past, from the interpretation target report.

4. The similar case searching apparatus according to claim 1, further comprising
    an image interpretation result extracting unit configured to extract, from the description related to the first test divided by the report analyzing unit, one or more image interpretation items each of which is a character string indicating a feature of a medical image, each of the image interpretation items indicating a feature of the interpretation target image obtained by carrying out the first test on the subject,
    wherein the two-data correlation information further indicates a correlation between each of the image feature quantities extracted from the one or more medical images and each of the image interpretation items extracted from the image interpretation report related to the one or more medical images, and
    the weight determining unit is configured to determine, for each of the image feature quantities extracted from the interpretation target image by the image feature quantity extracting unit, a weight based on the two-data correlation information, the weight having a value that is larger as the correlation between the image feature quantity and the image interpretation item extracted by the image interpretation result extracting unit or the reference expression extracted by the reference expression extracting unit is higher.

5. The similar case searching apparatus according to claim 4,
    wherein the image interpretation result extracting unit is further configured to extract one or more disease names each of which is a result of a diagnosis made by the user from the description related to the first test,
    the two-data correlation information further indicates a correlation between each of the image feature quantities extracted from the one or more medical images and each of the disease names extracted from the image interpretation report related to the one or more medical images, and
    the weight determining unit is configured to determine, for each of the image feature quantities extracted from the interpretation target image by the image feature quantity extracting unit, a weight based on the two-data correlation information, the weight having a value that is larger as the correlation between the image feature quantity and one of the image interpretation item or the disease name extracted by the image interpretation result extracting unit and the reference expression extracted by the reference expression extracting unit is higher.

6. The similar case searching apparatus according to claim 5,
wherein, when the image interpretation result extracting unit extracts the disease name from the description related to the first test, the weight determining unit is configured to determine, for each of the image feature quantities extracted from the interpretation target image by the image feature quantity extracting unit, a weight based on the two-data correlation information, the weight having a value that is larger as the correlation between the image feature quantity and the disease name extracted by the image interpretation result extracting unit is higher.

7. The similar case searching apparatus according to claim 4,
wherein the two-data correlation information further indicates a correlation between each of the image interpretation items and each of the disease names which are extracted from the image interpretation report, and
when (i) the image interpretation result extracting unit extracts the one or more disease names from the description related to the first test and (ii) the image interpretation result extracting unit extracts the one or more image interpretation items from the description related to the first test or the reference expression extracting unit extracts the one or more reference expressions from the description related to the second test, the weight determining unit is configured to determine, for each of the image feature quantities extracted from the interpretation target image by the image feature quantity extracting unit, a weight based on the two-data correlation information, the weight having a value that is a product of (i) a value indicating the correlation between the image feature quantity and the image interpretation items extracted by the image interpretation result extracting unit or the reference expression extracted by the reference expression extracting unit and (ii) a value indicating the correlation between the image interpretation items or the reference expression and the disease name extracted by the image interpretation result extracting unit.

8. The similar case searching apparatus according to claim 4,
wherein, when (i) the image interpretation result extracting unit extracts one of the image interpretation items from the description related to the first test or (ii) the reference expression extracting unit extracts one of the reference expressions from the description related to the second test, the weight determining unit is configured to determine, for each of the image feature quantities extracted from the interpretation target image by the image feature quantity extracting unit, a weight based on the two-data correlation information, the weight having a value indicating the correlation between the image feature quantity and the image interpretation item extracted by the image interpretation result extracting unit or the reference expression extracted by the reference expression extracting unit.

9. The similar case searching apparatus according to claim 4,
wherein each of case data items registered in the case database further includes a reference image obtained by carrying out the second test on the subject of the first test,
the image feature quantity extracting unit is further configured to extract a plurality of image feature quantities from the reference image,
the weight determining unit is further configured to determine, for each of the image feature quantities extracted from the reference image by the image feature quantity extracting unit, a weight based on the two-data correlation information, the weight having a value that is larger as the correlation between the image feature quantity and the image interpretation item extracted by the image interpretation result extracting unit or the reference expression extracted by the reference expression extracting unit is higher, and
the similar case searching unit is configured to search the case database for the similar case data item including similar images similar to the interpretation target image and the reference image, by weighting each of the image feature quantities in a first set extracted from the interpretation target image and the reference image by the image feature quantity extracting unit and the corresponding one of the image feature quantities in a second set extracted from the medical images included in the case data item registered in the case database, using the weight to the image feature quantity determined by the weight determining unit, and comparing the weighted image feature quantities in the first set and the weighted image feature quantities in the second set.

10. A similar case searching method of searching a case database for a similar case data item similar to a target case data item of a target case to be diagnosed, the case database storing a plurality of case data items, each of the case data items and the target case data item including one or more medical images and an image interpretation report that is a document data item indicating a result of interpreting the one or more medical images, the similar case searching method comprising:
extracting a plurality of image feature quantities from an interpretation target image which is a medical image and obtained by carrying out a first test on a subject;
analyzing a target image interpretation report which is generated by a user in interpretation of the interpretation target image, and dividing descriptions in the target image interpretation report into a description related to the first test and a description related to a second test different from the first test carried out on the subject of the first test;
extracting, from the description related to the second test, one or more reference expressions each of which is a character string indicating a feature of a medical image, each of the reference expressions indicating a feature of a reference image obtained by carrying out the second test on the subject of the first test;
determining, for each of the image feature quantities extracted from the interpretation target image, a weight based on two-data correlation information that is prepared information defining a correlation between each of image feature quantities extracted from one or more medical images and each of one or more reference expressions extracted from an image interpretation report of the one or more medical images, the weight to the extracted image feature quantity having a value that is larger as the correlation between the image feature quantity and the reference expression extracted from the description related to the second test is higher; and searching the case database for the similar case data item including a similar image similar to the interpretation target image, by weighting each of the image feature quantities in a first set extracted from the interpretation target image and a corresponding one of the image feature quantities in a second set extracted from the one or more medical images included in the case data item registered in the case database, using the weight to each of the determined image feature quantities, and comparing the weighted image feature quantities in the first set and the weighted image feature quantities in the second set.

11. A non-transitory computer-readable recording medium storing a program for causing a computer to execute the similar case searching method according to claim 10.

\* \* \* \* \*